(12) United States Patent
Liu et al.

(10) Patent No.: US 7,553,833 B2
(45) Date of Patent: Jun. 30, 2009

(54) 3,3-SPIROINDOLINONE DERIVATIVES

(75) Inventors: Jin-Jun Liu, Warren Township, NJ (US); Jefferson Wright Tilley, North Caldwell, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/101,182

(22) Filed: Apr. 11, 2008

(65) Prior Publication Data

US 2008/0287421 A1    Nov. 20, 2008

Related U.S. Application Data

(60) Provisional application No. 60/938,494, filed on May 17, 2007.

(51) Int. Cl.
C07D 487/10 (2006.01)
A61K 31/55 (2006.01)

(52) U.S. Cl. .................. 514/212.02; 540/521
(58) Field of Classification Search ............. 540/521; 514/212.02
See application file for complete search history.

(56) References Cited

FOREIGN PATENT DOCUMENTS

EP      0947511      10/1999

OTHER PUBLICATIONS

Howard C. Ansel, Pharmaceutical Dosage Forms and Drug Delivery Systems, 6th Ed. 1995, pp. 196, 456-457.
Lippa, B. et al, *Bioorganic & Med. Chem. Letters*, 18(11), (2008) 3359-3363 XP022711228.

*Primary Examiner*—Bruck Kifle
(74) *Attorney, Agent, or Firm*—George W. Johnston; Patricia S. Rocha-Tramaloni

(57) ABSTRACT

There are provided compounds of the general formulas

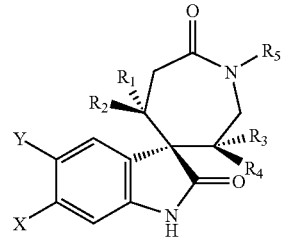

wherein X, Y, $R_1$, $R_2$, $R_3$, $R_4$ and $R_5$ are as described herein. The compounds exhibit anticancer activity.

8 Claims, No Drawings

3,3-SPIROINDOLINONE DERIVATIVES

PRIORITY TO RELATED APPLICATION(S)

This application claims the benefit of U.S. Provisional Application No. 60/938,494, filed May 17, 2007, which is hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to oxindole derivatives which act as antagonists of mdm2 interactions and hence are useful as potent and selective anticancer agents. The present compounds are of the general formulas

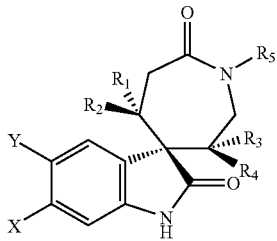

wherein X, Y, $R_1$, $R_2$, $R_3$, $R_4$ and $R_5$ are as described herein and enantiomers and pharmaceutically acceptable salts and esters thereof.

DETAILED DESCRIPTION OF THE INVENTION

There are provided compounds of the formula

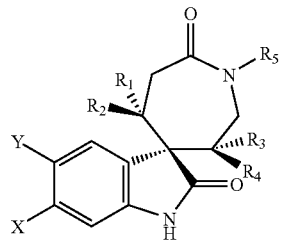

wherein
X is selected from the group consisting of hydrogen, halogen, cyano, nitro, ethynyl and cyclopropyl,
Y is hydrogen,
$R_1$, $R_2$, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl and substituted cycloalkenyl, with the proviso that one of $R_1/R_2$ or $R_3/R_4$ is hydrogen and the other not hydrogen and
$R_5$ is hydrogen, lower alkyl or substituted lower alkyl, and the pharmaceutically acceptable salts and esters thereof.
Preferred are compounds of formula I wherein
X is halogen,
Y is hydrogen,
$R_2$ is hydrogen,
$R_4$ is hydrogen,
$R_1$ and $R_3$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_3$ is a meta-halogen substituted phenyl with or without further substitution and
$R_5$ is hydrogen, lower alkyl or substituted lower alkyl.
Further preferred are compounds of formula I wherein
X is F, Cl or Br,
Y is hydrogen,
$R_2$ is hydrogen,
$R_4$ is hydrogen,
one of $R_1/R_3$ is a meta-halogen substituted phenyl with or without further substitution and the other of $R_1/R_3$ is selected from the group consisting of lower alkyl, lower alkenyl, aryl and substituted aryl and
$R_5$ is hydrogen, lower alkyl or substituted lower alkyl.
Especially preferred are compounds selected from the group consisting of
rac-(3S,4R,5S)-6'-chloro-3-(3-chlorophenyl)-1,1',2,2',3,5,6,7-octahydro-5-methoxy-spiro[4H-azepine-4,3'-[3H]-indole]-2',7-dione
rac-(3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione
(3R,4S,5S)-6'-chloro-5-(3-chlorophenyl)-1,1',2,2',3,5,6,7-octahydro-3-(1-methylethenylspiro[4H-azepine-4,3'-[3H]-indole]-2',7-dione (3S,4R,5R)-6'-chloro-3-(3-chlorophenyl)-1,1',2,2',3,5,6,7-octahydro-5-(1-methylethenylspiro[4H-azepine-4,3'-[3H]-indole]-2',7-dione rac-(3S,4R,5R)-6'-chloro-3,5-bis-(3-chlorophenyl)-1,1',2,2',3,5,6,7-octahydrospiro[4H-azepine-4,3'-[3H]-indole]-2',7-dione (3R,4S,5S)-6'-chloro-5-(3-chlorophenyl)-1,1',2,2',3,5,6,7-octahydro-3(E)-(1-methyl-1-propenyl)-spiro[4H-azepine-4,3'-[3H]-indole]-2',7-dione (3S,4R,5R)-6'-chloro-3-(3-chlorophenyl)-1,1',2,2',3,5,6,7-octahydro-5(E)-(1-methyl-1-propenyl)-spiro[4H-azepine-4,3'-[3H]-indole]-2',7-dione rac-(3S,4R,5S)-6'-chloro-3-(4-chlorophenyl)-1,1',2,2',3,5,6,7-octahydro-5-methoxy-spiro[4H-azepine-4,3'-[3H]-indole]-2',7-dione rac-(3R,4R,5S)-6'-chloro-5-(4-chlorophenyl)-1,1',2,2',3,5,6,7-octahydro-3-methoxy-spiro[4H-azepine-4,3'-[3H]-indole]-2',7-dione (3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione (3S,4R,5R)-6'-chloro-3-(3-chlorophenyl)-1,1',2,2',3,5,6,7-octahydro 5-(3-methylphenyl)-spiro[4H-azepine-4,3'-[3H]-indole]-2',7-dione (3R,4S,5S)-6'-chloro-5-(3-chlorophenyl)-1,1',2,2',3,5,6,7-octahydro-3-(3-methylphenyl)-spiro[4H-azepine-4,3'-[3H]-indole]-2',7-dione (3R,4S,5S)-6'-chloro-5-(3-chlorophenyl)-1,1',2,2',3,5,6,7-octahydro-3-(2-methylphenyl)-spiro[4H-azepine-4,3'-[3H]-indole]-2',7-dione (3S,4R,5R)-6'-chloro-3-(3-chlorophenyl)-1,1',2,2',3,5,6,7-octahydro-5-(2-methylphenyl)-spiro[4H-azepine-4,3'-[3H]-indole]-2',7-dione (3R,4S,5R)-6'-chloro-5-(3-chlorophenyl)-1,1',2,2',3,5,6,7-octahydro-3-(2-methylpropyl)-spiro[4H-azepine-4,3'-[3H]-indole]-2',7-dione (3S,4R,5S)-6'-chloro-3-(3-chlorophenyl)-1,1',2,2',3,5,6,7-octahydro-5-(2-methylpropyl)-spiro[4H-azepine-4,3'-[3H]-indole]-2',7-dione (3R,4S,5S)-6'-chloro-5-(3-chlorophenyl)-3-cyclopropyl-1,1',2,2',3,5,6,7-octahydrospiro[4H-azepine-4,3'-[3H]-indole]-2',7-dione (3S,4R,5R)-6'-chloro-3-(3-chlorophenyl)-5-cyclopropyl-1,1',2,2',3,5,6,7-octahydrospiro[4H-azepine-4,3'-[3H]-indole]-2',7-dione (3R,4S,5R)-6'-chloro-5-(3-chlorophenyl)-1,1',2,2',3,5,6,7-octahydro-3-(1-methylethyl)-spiro[4H-azepine-4,3'-[3H]-indole]-2',7-dione (3S,4R,5R)-6'-chloro-3-(3-chlorophenyl)-1,1',2,2',3,5,6,7-octahydro-5-(1-methylethyl)-spiro[4H-azepine-4,3'-[3H]-indole]-2',7-dione (3R,4S,5S)-6'-chloro-5-(3-chlorophenyl)-3-(5-fluoro-2-methylphenyl)-1,1',2,2',3,5,6,7-octahydrospiro[4H-azepine-4,3'-[3H]-indole]-2',7-dione (3S,4R,5R)-6'-chloro-3-(3-chlorophenyl)-5-(5-fluoro-2-methylphenyl)-1,1',2,2',3,5,6,7-octahydrospiro[4H-azepine-4,3'-[3H]-indole]-2',7-dione (3R,4S,5S)-6'-chloro-5-(3-chlorophenyl)-1,1',2,2',3,5,6,7-octahydro-3-phenyl-spiro[4H-azepine-4,3'-[3H]-indole]-2',7-dione (3S,4R,5R)-6'-chloro-3-(3-chlorophenyl)-1,1',2,2',3,5,6,7-octahydro-3-phenyl-spiro[4H-azepine-4,3'-[3H]-indole]-2',7-dione rac-(3S,4R,5S)-6'-bromo-3-(3-chlorophenyl)-1,1',2,2',3,5,6,7-octahydro-5-methoxy-spiro[4H-azepine-4,3'-[3H]-indole]-2',7-dione rac-(3R,4R,5S)-6'-bromo-5-(3-chlorophenyl)-1,1',2,2',3,5,6,7-octahydro-3-methoxy-spiro[4H-azepine-4,3'-[3H]-indole]-2',7-dione (3R,4S,5S)-6'-bromo-5-(3-chlorophenyl)-1,1',2,2',3,5,6,7-octahydro-3-(1-methylethenylspiro[4H-azepine-4,3'-[3H]-indole]-2',7-dione (3S,4R,5R)-6'-bromo-3-(3-chlorophenyl)-1,1',2,2',3,5,6,7-octahydro-5-(1-methylethenylspiro[4H-azepine-4,3'-[3H]-indole]-2',7-dione rac-(3S,4R,5S)-4'-chloro-3-(3-chlorophenyl)-1,1',2,2',3,5,6,7-octahydro-5-methoxy-1-methyl-spiro[4H-azepine-4,3'-[3H]-indole]-2',7-dione rac-(3R,4R,5S)-6'-chloro-5-(3-chlorophenyl)-1,1',2,2',3,5,6,7-octahydro-3-methoxy-1-methyl-spiro[4H-azepine-4,3'-[3H]-indole]-2',7-dione rac-(3S,4R,5R)-6'-chloro-3-(3-chlorophenyl)-1-ethyl-1,1',2,2',3,5,6,7-octahydro-5-methoxy-spiro[4H-azepine-4,3'-[3H]-indole]-2',7-dione rac-(3R,4R,5S)-6'-chloro-5-(3-chlorophenyl)-1-ethyl-1,1',2,2',3,5,6,7-octahydro-3-methoxy-spiro[4H-azepine-4,3'-[3H]-indole]-2',7-dione (3R,4R,5S)-6'-chloro-5-(3-chlorophenyl)-3-ethoxyl-1,1',2,2',3,5,6,7-octahydrospiro[4H-azepine-4,3'-[3H]-indole]-2',7-dione (3S,4R,5S)-6'-chloro-3-(3-chlorophenyl)-5-ethoxy-1,1',2,2',3,5,6,7-octahydrospiro[4H-azepine-4,3'-[3H]-indole]-2',7-dione (3R,4R,5S)-6'-chloro-5-(3-chlorophenyl)-1,1',2,2',3,5,6,7-octahydro-3-(1-methylethoxy)-spiro[4H-azepine-4,3'-[3H]-indole]-2',7-dione (3S,4R,5S)-6'-chloro-3-(3-chlorophenyl)-1,1',2,2',3,5,6,7-octahydro-5-(1-methylethoxy)-spiro[4H-azepine-4,3'-[3H]-indole]-2',7-dione 3S,4R,5S)-6'-chloro-3-(3-chlorophenyl)-5-(2,2-dimethylpropoxy)-1,1',2,2',3,5,6,7-octahydrospiro[4H-azepine-4,3'-[3H]-indole]-2',7-dione (3R,4R,5S)-6'-chloro-5-(3-chlorophenyl)-3-(2,2-dimethylpropoxy)-1,1',2,2',3,5,6,7-octahydrospiro[4H-azepine-4,3'-[3H]-indole]-2',7-dione The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-$_2$-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, carboxy, carboxy lower alkoxy and CN. Preferred substituents for alkyl are alkoxy and N(lower alkyl)$_2$.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula Ia and Ib as well as their salts that have at least one asymmetric carbon atom may be present as racemic mixtures or different stereoisomers. The various isomers can be isolated by known separation methods, e.g., chromatography.

Compounds disclosed herein and covered by formula Ia and Ib above may exhibit tautomerism or structural isomerism. It is intended that the invention encompasses any tautomeric or structural isomeric form of these compounds, or mixtures of such forms, and is not limited to any one tautomeric or structural isomeric form depicted in formula Ia and Ib above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

Synthetic Methods

The present invention provides methods for the synthesis of spiroindolinones. The compounds of the invention can be prepared by processes known in the art. Suitable processes for synthesizing these compounds are provided in the examples. Generally, the compounds of the invention can be prepared according to the synthesis schemes provided below.

The following synthetic schemes provide three general methods for preparation of compounds of the invention, i.e., compounds of formula I. In method A, illustrated in scheme 1, a compound of formula II is converted to a compound of formula I by heating with NaN3 in the presence of acid catalyst.

Scheme 1

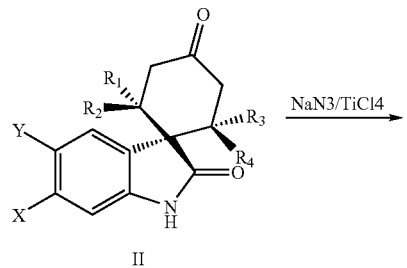

II

-continued

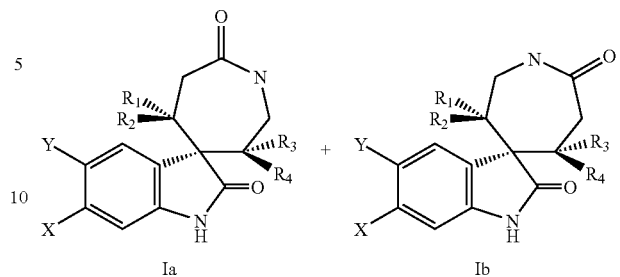

Ia    Ib

In method B, shown in schemes 2, a compound of formula II is converted to a compound of formula I by reacting with NH2OH—HCl and p-TsCl to form oxime intermediates III and IV followed by heating under microwave irradiation in the presence of acid catalyst.

Scheme 2

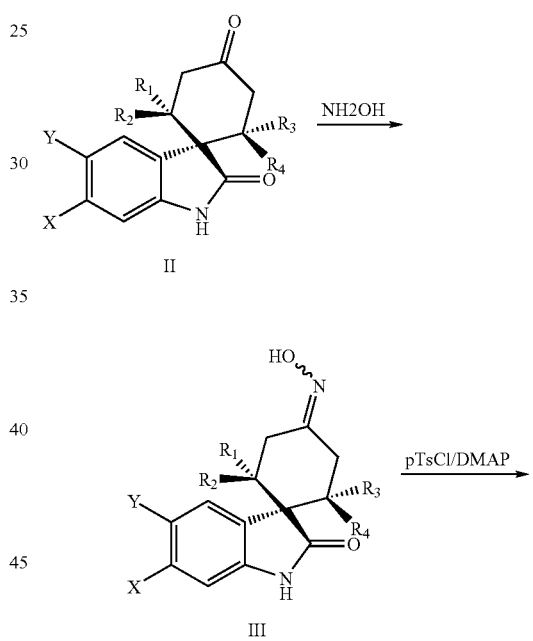

II

III

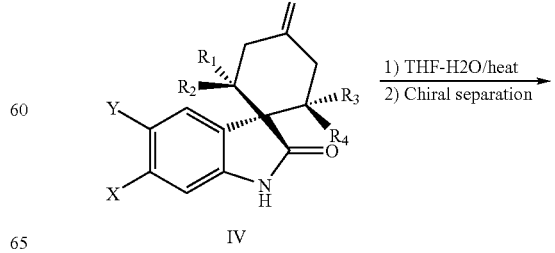

IV

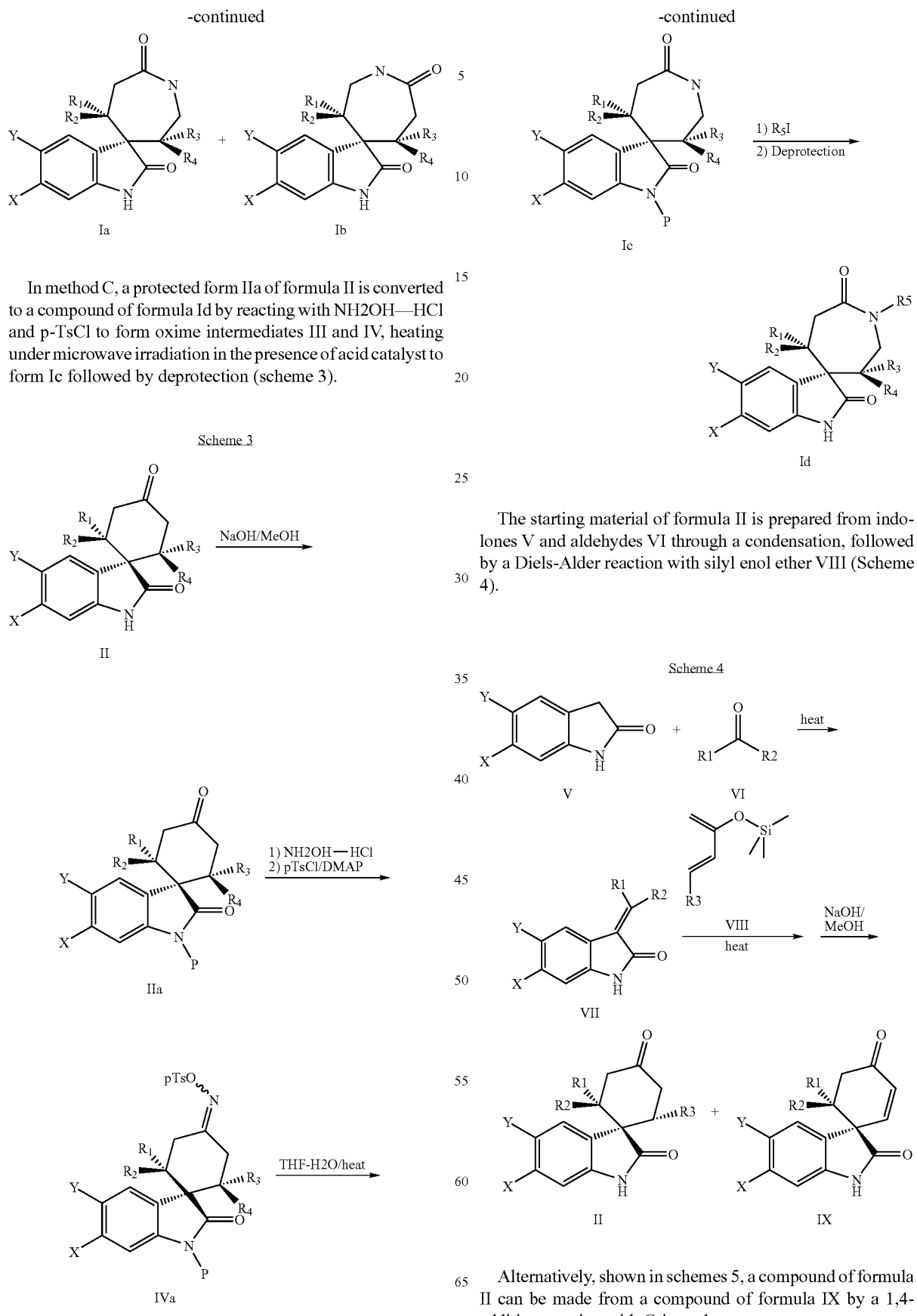

In method C, a protected form IIa of formula II is converted to a compound of formula Id by reacting with NH2OH—HCl and p-TsCl to form oxime intermediates III and IV, heating under microwave irradiation in the presence of acid catalyst to form Ic followed by deprotection (scheme 3).

The starting material of formula II is prepared from indolones V and aldehydes VI through a condensation, followed by a Diels-Alder reaction with silyl enol ether VIII (Scheme 4).

Alternatively, shown in schemes 5, a compound of formula II can be made from a compound of formula IX by a 1,4-addition reaction with Grignard reagent.

11

Scheme 5

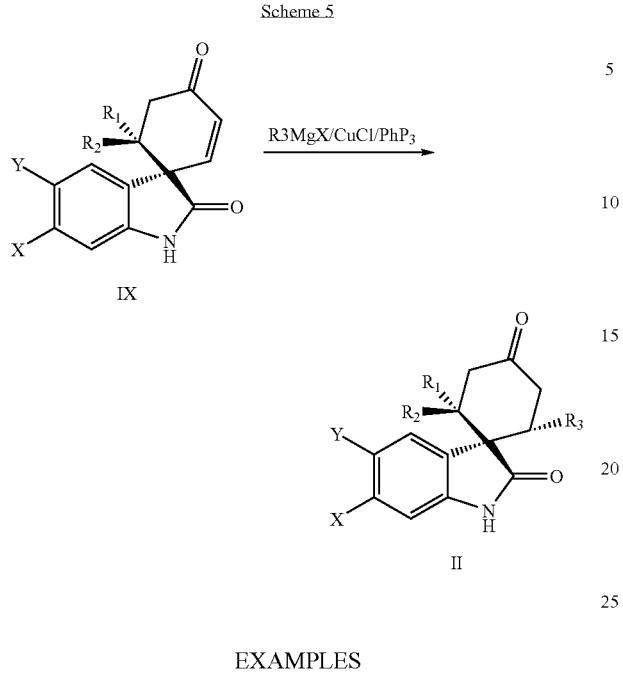

EXAMPLES

The compounds of the present invention may be synthesized according to known techniques. The following examples and references are provided to aid the understanding of the present invention, the true scope of which is set forth in the appended claims.

Example 1

General Synthesis Steps and Starting Materials

Example 1a

Preparation of Intermediate E/Z-substituted-methylidene]-1,3-dihydro-indol-2-one VII

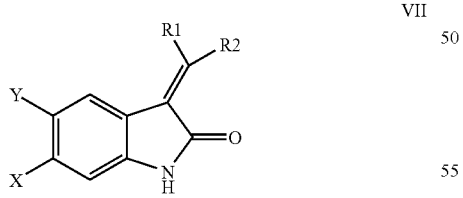

To the mixture of appropriate oxindole (92 mmol) and aldehyde (92 mmol) in methanol (100 mL) was added pyrrolidine (92 mmol) dropwise. The mixture was then heated at 70° C. for 3 h. After cooled to 4° C., the mixture was filtered and resulting precipitate was collected, dried to give a mixture of E/Z-substituted-methylidene]-1,3-dihydro-indol-2-one VII (>90%).

12

Example 1b

Preparation of Rac-(6-alkooxyspiro[cyclohexane-1,3'-[3H]indole]-2',4(1'H)-dione II and Rac-spiro[5-cyclohexene-1,3'-[3H]indole]-2',4(1'H)-dione IX (scheme 4).

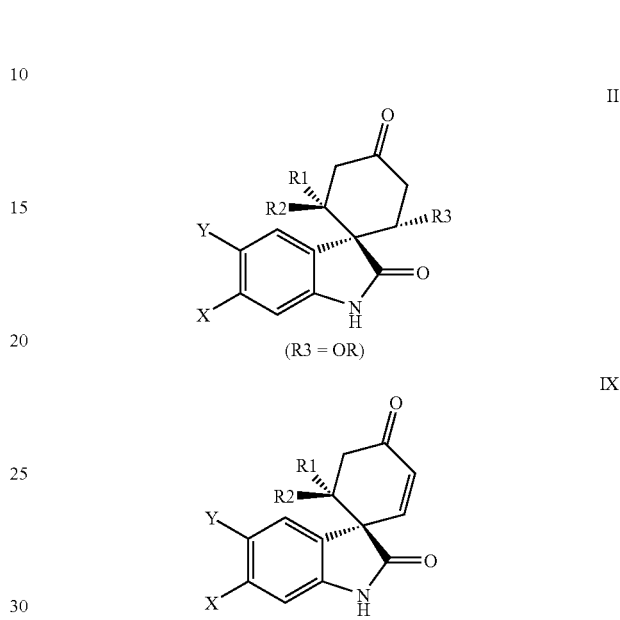

To a suspension of E/Z-substituted-methylidene]-1,3-dihydro-indol-2-one VII (15.0 mmol) in toluene (50 mL) in a sealed tube was added (3-methoxy-1-methylene-allyloxy)-trimethyl-silane (3.44 g, 20.0 mmol). The reaction mixture was allowed to stir at 140° C. for 24 hrs. The solvent was removed by concentration. The residue was dissolved in MeOH (50 mL) and treated with 4 N NaOH (5 mL) at rt for 2 hrs. The reaction mixture was then diluted with AcOEt and washed with water and brine. After concentration the residue was purified by flash column to give rac-(6-alkooxyspiro[cyclohexane-1,3'-[3H]indole]-2',4(1'H)-dione II and rac-spiro[5-cyclohexene-1,3'-[3H]indole]-2',4(1'H)-dione IX

Example 1c

Preparation of Rac-(6-substituted-spiro[cyclohexane-1,3'-[3H]indole]-2',4(1'H)-dione II from Rac-spiro[5-cyclohexene-1,3'-[3H]indole]-2',4(1'H)-dione IX (scheme 5)

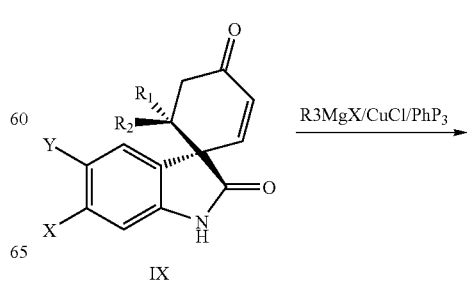

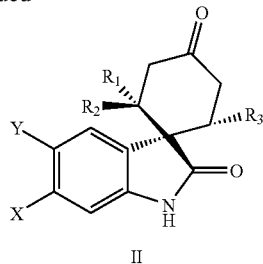

II

In a flask equipped with septum and stirring bar, a mixture of CuCl (17.6 mg, 0.18 mmol) and Ph₃P (76.1 mg, 0.21 mmol) was suspended in THF (2 mL). After stirring under argon at rt for 30 min, rac-spiro[5-cyclohexene-1,3'-[3H]indole]-2',4(1'H)-dione IX (0.28 mmol) was added in one portion. After additional stirring for 10 min, R3MgX (0.84 mmol) was added dropwise to the resulting mixture during 5 min at 0° C. After stirring under argon at 0° C. to −10° C. for 1 h, the reaction mixture was allowed to stir overnight with the ice-bath. Sat.NH4Cl was then added to the reaction mixture. The organic phase was separated. The mixture was then separated by flash column to give rac-(6-substituted-spiro[cyclohexane-1,3'-[3H]indole]-2',4(1'H)-dione II*

Example 2

General Procedure for the Preparation of Compounds I

Method A

Preparation of compounds I from Rac-(6-substituted)-spiro[cyclohexane-1,3'-[3H]indole]-2',4(1'H)-dione II via Titanium Chloride-mediated ring extension

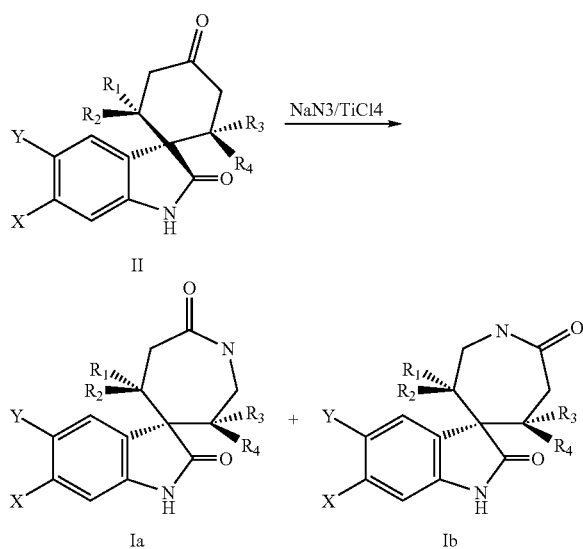

To a suspension of appropriate rac-(6-substituted)-spiro[cyclohexane-1,3'-[3H]indole]-2',4(1'H)-dione II (0.29 mmole) and NaN3 (0.72 mmole) in MeCN (10 mL) was added TiCl₄ (0.29 mmole) and the reaction mixture was allowed to reflux for 6-8 hrs. The reaction was quenched by adding Sat. NaHCO3 after cooled to rt. The reaction mixture was extracted with AcOEt and the solvent was removed by concentration. The residue was purified by flash column (15%-100% AcOEt in Hex) to give a mixture of Ia and Ib. The mixture was further separated by either a regular flash column to give racemic forms of compound Ia and Ib, or a chiral column to give pure entantiomers of compound Ia and Ib.

Method B

Preparation of compounds I from Rac-(6-substituted)-spiro[cyclohexane-1,3'-[3H]indole]-2',4(1'H)-dione II via Titanium Chloride-mediated ring extension (scheme 4)

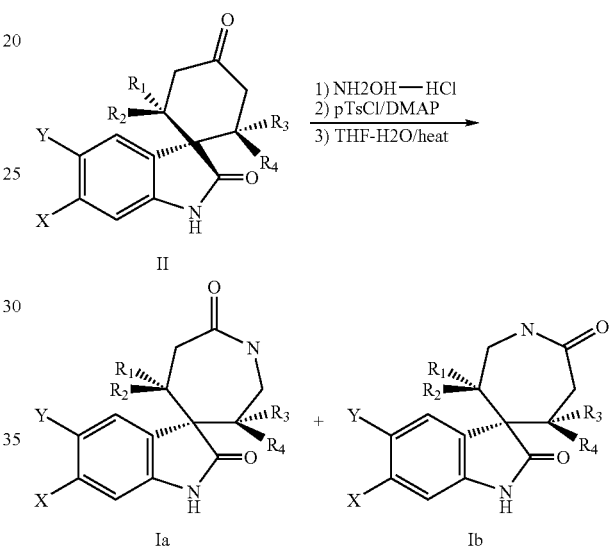

Step 1

A suspension of Rac-(6-substituted)-spiro[cyclohexane-1,3'-[3H]indole]-2',4(1'H)-dione II (0.52 mmol), NaOH (0.52 mmole) and NH₂OH—HCl (0.52 mmol) in EtOH-water (3/2, 20 mL) was allowed to reflux for 1-3 hrs. The reaction was cooled to room temperature, and water was added. The mixture was extracted with ethyl acetate. The organic layer was separated, dried over MgSO₄, and concentrated. The residue was purified by chromatography to give the corresponding oxime as a white solid.

Step 2

To the solution of rac-E/Z-spiro[cyclohexane-1,3'-[3H]indole]-2',4(1'H)-dione-4-oxime obtained above (0.39 mmol) and DMAP (0.78 mmol) in dichloromethane (3 mL) was added a solution of p-toluenesulfonyl chloride (0.39 mmol) in dichloromethane (2 mL) at room temperature. The reaction mixture was stirred at room temperature for 1 h. The reaction was then concentrated and the residue was purified by chromatography to give the corresponding E and Z isomers of the spiro[cyclohexane-1,3'-[3H]indole]-2',4(1'H)-dione-4-(O-p-toulenesulfonyl)-oximes as a white solid.

Step 3

Rac-Z or E spiro[cyclohexane-1,3'-[3H]indole]-2',4(1'H)-dione-4-(O-p-toulenesulfonyl)-oxime (1 mmol) prepared in step 2 was dissolved in THF/H₂O (10/5 mL) and heated in a sealed tube under microwave irradiation at 100° C. for 30 min. After diluted with AcOEt the mixture was washed with water, dried over Na₂SO₄ and concentrated. The residue was purified by chromatography to give the corresponding rac-spiro[3H-indole-3,4'-azopane]-2,7'(1'H)-dione Ia or Ib which can be further separated by chiral column chromatography to give pure entantiomers of compound Ia and Ib.

Example 3

Preparation of rac-(3S,4R,5S)-6'-chloro-3-(3-chlorophenyl)-1,1',2,2',3,5,6,7-octahydro-5-methoxy-spiro[4H-azepine-4,3'-[3H]-indole]-2',7-dione and rac-(3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione

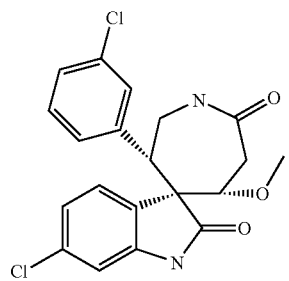

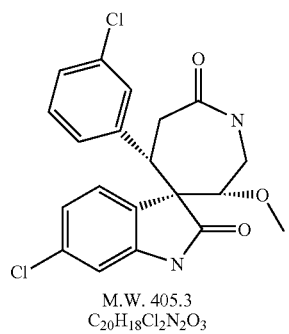

M.W. 405.3
C₂₀H₁₈Cl₂N₂O₃

In a manner similar to the method described in example 2 (method A), rac-(1R,2S,6S)-6'-chloro-2-(3-chlorophenyl)-6-methoxyspiro[cyclohexane-1,3'-[3H]indole]-2',4(1'H)-dione (156 mg, 0.4 mmol) was reacted with NaN3 (52 mg, 0.8 mmole) in the presence of TiCl4 (1.0 M in CH₂Cl₂, 0.8 mL) (Aldrich) in acetonitrile (10 mL) to give rac-(3S,4R,5S)-6'-chloro-3-(3-chlorophenyl)-1,1',2,2',3,5,6,7-octahydro-5-methoxy-spiro[4H-azepine-4,3'-[3H]-indole]-2',7-dione (25.3 mg): HRMS (ES⁺) m/z Calcd for C₂₀H₁₈Cl₂N₂O₃+H [(M+H)⁺]: 405.0767, found: 405.0765 and rac-(3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione: HRMS (ES⁺) m/z Calcd for C₂₀H₁₈Cl₂N₂O₃+H [(M+H)⁺]: 405.0767, found: 405.0768.

Example 4

Preparation of (3S,4R,5R)-6'-chloro-5-(3-chlorophenyl)-1,1',2,2',3,5,6,7-octahydro-3-(1-methylethenyl)-spiro[4H-azepine-4,3'-[3H]-indole]-2',7-dione, (3R,4S,5S)-6'-chloro-5-(3-chlorophenyl))-1,1',2,2',3,5,6,7-octahydro-3-(1-methylethenylspiro[4H-azepine-4,3'-[3H]-indole]-2',7-dione, (3S,4R,5R)-6'-chloro-3-(3-chlorophenyl))-1,1',2,2',3,5,6,7-octahydro-5-(1-methylethenylspiro[4H-azepine-4,3'-[3H]-indole]-2',7-dione and (3R,4S,5S)-6'-chloro-3-(3-chlorophenyl)-1,1',2,2',3,5,6,7-octahydro-5-(1-methylethenyl)-spiro[4H-azepine-4,3'-[3H]-indole]-2',7-dione

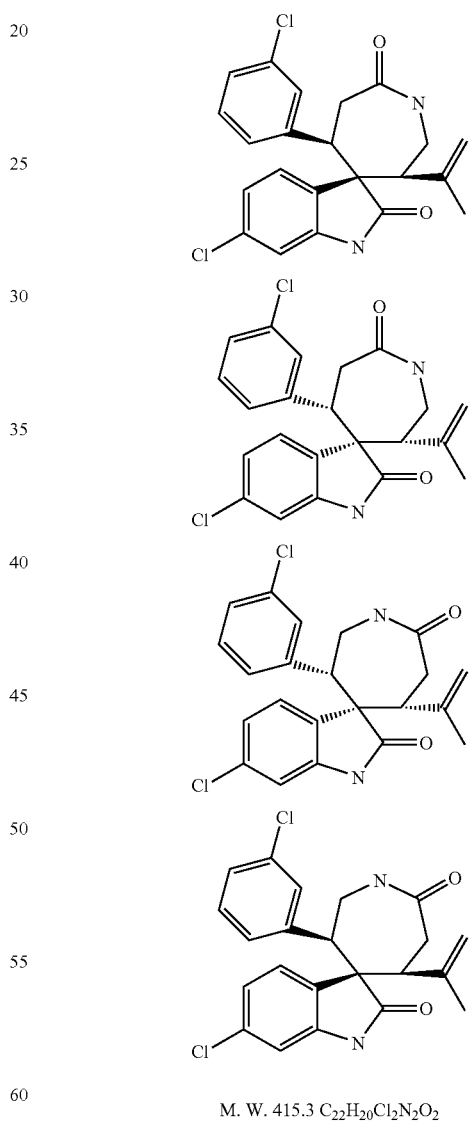

M. W. 415.3 C₂₂H₂₀Cl₂N₂O₂

In a manner similar to the method described in example 2 (method A), rac-(1R,2S,6R)-6'-chloro-2-(3-chlorophenyl)-6-iso-propenylspiro[cyclohexane-1,3'-[3H]indole]-2',4(1'H)-dione (120 mg, 0.3 mmol) was reacted with NaN3 (39 mg, 0.6 mmole) in the presence of TiCl4 (1.0 M in CH$_2$Cl$_2$, 0.3 mL) (Aldrich) in acetonitrile (10 mL) followed by chiral chromatography separation to give (3S,4R,5R)-6'-chloro-5-(3-chlorophenyl)-1,1',2,2',3,5,6,7-octahydro-3-(1-methylethenyl)-spiro[4H-azepine-4,3'-[3H]-indole]-2',7-dione (25.9 mg): HRMS (ES$^+$) m/z Calcd for C$_{22}$H$_{20}$Cl$_2$N$_2$O$_2$+H [(M+H)$^+$]: 415.0975, Found: 415.0974; (3R,4S,5S)-6'-chloro-5-(3-chlorophenyl))-1,1',2,2',3,5,6,7-octahydro-3-(1-methylethenylspiro[4H-azepine-4,3'-[3H]-indole]-2',7-dione (28.8 mg): HRMS (ES$^+$) m/z Calcd for C$_{22}$H$_{20}$Cl$_2$N$_2$O$_2$+H [(M+H)$^+$]: 415.0975, found: 415.0975; (3S,4R,5R)-4'-chloro-3-(3-chlorophenyl))-1,1',2,2',3,5,6,7-octahydro-5-(1-methylethenyl-spiro[4H-azepine-4,3'-[3H]-indole]-2',7-dione (20.7 mg): HRMS (ES$^+$) m/z Calcd for C$_{22}$H$_{20}$Cl$_2$N$_2$O$_2$+H [(M+H)$^+$]: 415.0975, found: 415.0974; and (3R,4S,5S)-6'-chloro-3-(3-chlorophenyl)-1,1',2,2',3,5,6,7-octahydro-5-(1-methylethenyl)-spiro[4H-azepine-4,3'-[3H]-indole]-2',7-dione (21.6 mg): HRMS (ES$^+$) m/z Calcd for C$_{22}$H$_{20}$Cl$_2$N$_2$O$_2$+H [(M+H)$^+$]: 415.0975, found: 415.0974.

Example 5

Preparation of rac-(3S,4R,5R)-6'-chloro-3,5-bis-(3-chlorophenyl)-1,1',2,2',3,5,6,7-octahydrospiro[4H-azepine-4,3'-[3H]-indole]-2',7-dione

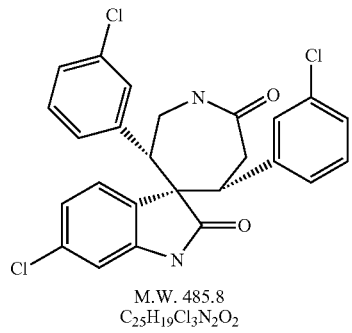

M.W. 485.8
C$_{25}$H$_{19}$Cl$_3$N$_2$O$_2$

In a manner similar to the method described in example 2 (method A), rac-(1R,2S,6S)-4'-chloro-2-(3-chlorophenyl)-4-(3-chlorophenyl)-spiro[cyclohexane-1,3'-[3H]indole]-2',4(1'H)-dione (141 mg, 0.3 mmol) was reacted with NaN3 (39 mg, 0.6 mmole) in the presence of TiCl4 (1.0 M in CH$_2$Cl$_2$, 0.3 mL) (Aldrich) in acetonitrile (10 mL) to give rac-(3S,4R,5R)-6'-chloro-3,5-bis-(3-chlorophenyl)-1,1',2,2',3,5,6,7-octahydrospiro[4H-azepine-4,3'-[3H]-indole]-2',7-dione: HRMS (ES$^+$) m/z Calcd for C$_{25}$H$_{19}$Cl$_3$N$_2$O$_2$+H [(M+H)$^+$]: 485.0585, found: 485.0585.

Example 6

Preparation of (3R,4S,5S)-6'-chloro-3-(3-chlorophenyl)-1,1',2,2',3,5,6,7-octahydro-5(E)-(1-methyl-1-propenyl)-spiro[4H-azepine-4,3'-[3H]-indole]-2',7-dione; (3R,4S,5S)-6'-chloro-5-(3-chlorophenyl)-1,1',2,2',3,5,6,7-octahydro-3(E)-(1-methyl-1-propenyl)-spiro[4H-azepine-4,3'-[3H]-indole]-2',7-dione; (3S,4R,5R)-6'-chloro-3-(3-chlorophenyl)-1,1',2,2',3,5,6,7-octahydro-5(E)-(1-methyl-1-propenyl)-spiro[4H-azepine-4,3'-[3H]-indole]-2',7-dione and (3S,4R,5R)-6'-chloro-5-(3-chlorophenyl)-1,1',2,2',3,5,6,7-octahydro-3(E)-(1-methyl-1-propenyl)-spiro[4H-azepine-4,3'-[3H]-indole]-2',7-dione M.W. 429.3
C$_{23}$H$_{22}$Cl$_2$N$_2$O$_2$ In a manner similar to the method described in example 2 (method A), rac-(1R,2S,6R)-6'-chloro-2-(3-chlorophenyl)-6-(1-methyl-propenyl)spiro[cyclohexane-1,3'-[3H]indole]-2',4(1'H)-dione (120 mg, 0.29 mmol) was reacted with NaN3 (47.1 mg, 0.72 mmole) in the presence of TiCl4 (1.0 M in CH$_2$Cl$_2$, 0.29 mL) (Aldrich) in acetonitrile (10 mL) followed by chiral chromatography separation to give 3R,4S,5S)-6'-chloro-3-(3-chlorophenyl)-1,1',2,2',3,5,6,7-octahydro-5(E)-(1-methyl-1-propenyl)-spiro[4H-azepine-4,3'-[3H]-indole]-2',7-dione (13.5 mg): HRMS (ES$^+$) m/z Calcd for C$_{23}$H$_{22}$Cl$_2$N$_2$O$_2$+H [(M+H)$^+$]: 429.1131. Found: 429.1131; (3R,4S,5S)-6'-chloro-5-(3-chlorophenyl)-1,1',2,2',3,5,6,7-octahydro-3(E)-(1-methyl-1-propenyl)-spiro[4H-azepine-4,3'-[3H]-indole]-2',7-dione (15.8 mg): HRMS (ES$^+$) m/z Calcd for C$_{23}$H$_{22}$Cl$_2$N$_2$O$_2$+H [(M+H)$^+$]: 429.1131. Found: 429.1131; (3S,4R,5R)-6'-chloro-3-(3-chlorophenyl)-1,1',2,2',3,5,6,7-octahydro-5(E)-(1-methyl-1-propenyl)-spiro[4H-azepine-4,3'-[3H]-indole]-2',7-dione (13.7 mg): HRMS (ES$^+$) m/z Calcd for C$_{23}$H$_{22}$Cl$_2$N$_2$O$_2$+H [(M+H)$^+$]: 429.1131. Found: 429.1131; and (3S,4R,5R)-6'-chloro-5-(3-chlorophenyl)-1,1',2,2',3,5,6,7-octahydro-3(E)-(1-methyl-1-propenyl)-spiro[4H-azepine-4,3'-[3H]-indole]-2',7-dione (14.5 mg): HRMS (ES$^+$) m/z Calcd for C$_{23}$H$_{22}$Cl$_2$N$_2$O$_2$+H [(M+H)$^+$]: 429.1131. Found: 429.1131.

Example 7

Preparation of rac-(3S,4R,5S)-6'-chloro-3-(4-chlorophenyl)-1,1',2,2',3,5,6,7-octahydro-5-methoxy-spiro[4H-azepine-4,3'-[3H]-indole]-2',7-dione and rac-(3R,4R,5S)-6'-chloro-5-(4-chlorophenyl)-1,1',2,2',3,5,6,7-octahydro-3-methoxy-spiro[4H-azepine-4,3'-[3H]-indole]-2',7-dione

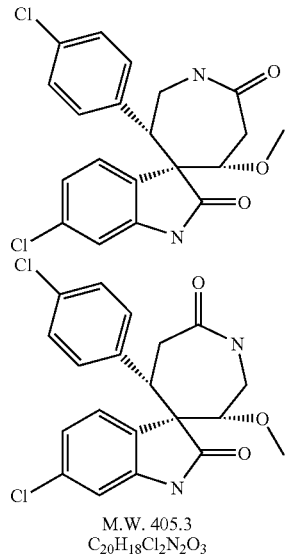

M.W. 405.3
C$_{20}$H$_{18}$Cl$_2$N$_2$O$_3$

In a manner similar to the method described in example 2 (method A), rac-(1R,2S,6S)-6'-chloro-2-(4-chlorophenyl)-6-methoxyspiro[cyclohexane-1,3'-[3H]indole]-2',4(1'H)-dione (312 mg, 0.8 mmol) was reacted with NaN3 (104 mg, 1.6 mmole) in the presence of TiCl4 (1.0 M in CH$_2$Cl$_2$, 0.8 mL) (Aldrich) in acetonitrile (20 mL) to give rac-(3S,4R,5S)-6'-chloro-3-(4-chlorophenyl)-1,1',2,2',3,5,6,7-octahydro-5-methoxy-spiro[4H-azepine-4,3'-[3H]-indole]-2',7-dione (18.6 mg): HRMS (ES$^+$) m/z Calcd for C$_{20}$H$_{18}$Cl$_2$N$_2$O$_3$+H [(M+H)$^+$]: 405.0767. Found: 405.0768; and rac-(3R,4R,5S)-6'-chloro-5-(4-chlorophenyl)-1,1',2,2',3,5,6,7-octahydro-3-methoxy-spiro[4H-azepine-4,3'-[3H]-indole]-2',7-dione (19.7 mg): HRMS (ES$^+$) m/z Calcd for C$_{20}$H$_{18}$Cl$_2$N$_2$O$_3$+H [(M+H)$^+$]: 405.0767. Found: 405.0768.

Example 8

Preparation of (3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione and (3S,4S,5R)-6'-chloro-5-(3-chlorophenyl)-1,1',2,2',3,5,6,7-octahydro-3-methoxy-spiro[4H-azepine-4,3'-[3H]-indole]-2',7-dione

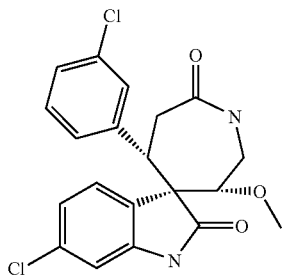

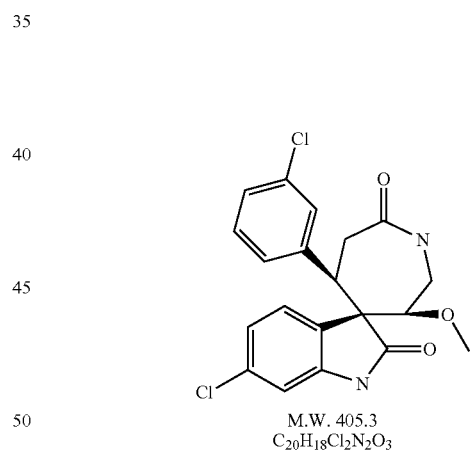

M.W. 405.3
C$_{20}$H$_{18}$Cl$_2$N$_2$O$_3$

In a manner similar to the method described in example 2 (method A), rac-(1R,2S,6S)-6'-chloro-2-(3-chlorophenyl)-6-methoxyspiro[cyclohexane-1,3'-[3H]indole]-2',4(1'H)-dione (156 mg, 0.4 mmol) was reacted with NaN3 (52 mg, 0.8 mmole) in the presence of TiCl4 (1.0 M in CH$_2$Cl$_2$, 0.8 mL) (Aldrich) in acetonitrile (10 mL) followed by chiral chromatograph to give (3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione (17.6 mg) and (3S,4S,5R)-6'-chloro-5-(3-chlorophenyl)-1,1',2,2',3,5,6,7-octahydro-3-methoxy-spiro[4H-azepine-4,3'-[3H]-indole]-2',7-dione.

Example 9

Preparation of (3S,4R,5R)-6'-chloro-3-(3-chlorophenyl)-1,1',2,2',3,5,6,7-octahydro-5-(3-methylphenyl)-spiro[4H-azepine-4,3'-[3H]-indole]-2',7-dione, (3S,4R,5R)-6'-chloro-5-(3-chlorophenyl)-1,1',2,2',3,5,6,7-octahydro-3-(3-methylphenyl)-spiro[4H-azepine-4,3'-[3H]-indole]-2',7-dione, (3R,4S,5S)-6'-chloro-3-(3-chlorophenyl)-1,1',2,2',3,5,6,7-octahydro-5-(3-methylphenyl)-spiro[4H-azepine-4,3'-[3H]-indole]-2',7-dione and (3R,4S,5S)-6'-chloro-5-(3-chlorophenyl)-1,1',2,2',3,5,6,7-octahydro-3-(3-methylphenyl)-spiro[4H-azepine-4,3'-[3H]-indole]-2',7-dione.

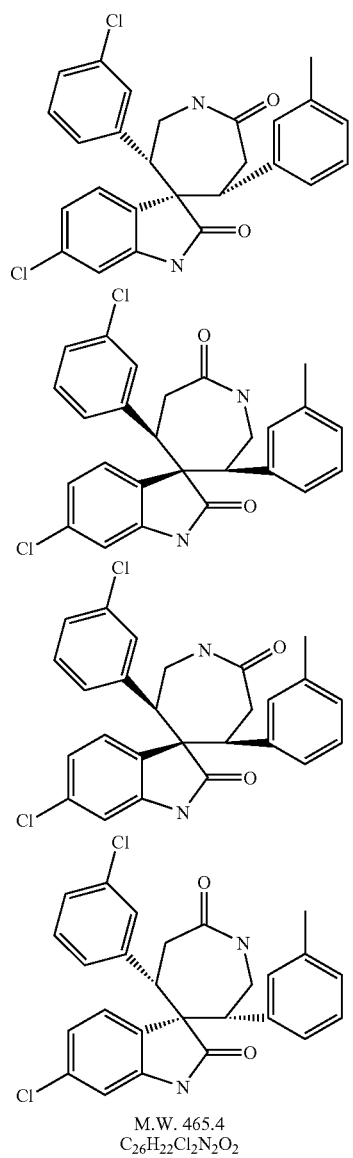

M.W. 465.4
$C_{26}H_{22}Cl_2N_2O_2$

In a manner similar to the method described in example 2 (method A), rac-(1R,2S,6R)-6'-chloro-2-(3-chlorophenyl)-6-(3-methylphenyl)spiro[cyclohexane-1,3'-[3H]indole]-2',4(1'H)-dione (140 mg, 0.31 mmol) was reacted with NaN3 (50.1 mg, 0.78 mmole) in the presence of TiCl4 (1.0 M in CH2Cl2, 0.31 mL) (Aldrich) in acetonitrile (10 mL) followed by chiral chromatograph to give (3S,4R,5R)-6'-chloro-3-(3-chlorophenyl)-1,1',2,2',3,5,6,7-octahydro-5-(3-methylphenyl)-spiro[4H-azepine-4,3'-[3H]-indole]-2',7-dione (11.2 mg): HRMS (ES+) m/z Calcd for $C_{26}H_{22}Cl_2N_2O_2$+H [(M+H)+]: 465.1131. Found: 465.1132; (3S,4R,5R)-6'-chloro-5-(3-chlorophenyl)-1,1',2,2',3,5,6,7-octahydro-3-(3-methylphenyl)-spiro[4H-azepine-4,3'-[3H]-indole]-2',7-dione (10.7 mg): HRMS (ES+) m/z Calcd for $C_{26}H_{22}Cl_2N_2O_2$+H [(M+H)+]: 465.1131. Found: 465.1131; (3R,4S,5S)-6'-chloro-3-(3-chlorophenyl)-1,1',2,2',3,5,6,7-octahydro-5-(3-methylphenyl)-spiro[4H-azepine-4,3'-[3H]-indole]-2',7-dione (10.3 mg): HRMS (ES+) m/z Calcd for $C_{26}H_{22}Cl_2N_2O_2$+H [(M+H)+]: 465.1131. Found: 465.1131; and (3R,4S,5S)-6'-chloro-5-(3-chlorophenyl)-1,1',2,2',3,5,6,7-octahydro-3-(3-methylphenyl)-spiro[4H-azepine-4,3'-[3H]-indole]-2',7-dione (10.1 mg): HRMS (ES+) m/z Calcd for $C_{26}H_{22}Cl_2N_2O_2$+H [(M+H)+]: 465.1131. Found: 465.1131.

Example 10

Preparation of (3R,4S,5S)-6'-chloro-5-(3-chlorophenyl)-1,1',2,2',3,5,6,7-octahydro-3-(2-methylphenyl)-spiro[4H-azepine-4,3'-[3H]-indole]-2',7-dione, (3R,4S,5S)-6'-chloro-3-(3-chlorophenyl)-1,1',2,2',3,5,6,7-octahydro-5-(2-methylphenyl)-spiro[4H-azepine-4,3'-[3H]-indole]-2',7-dione, (3S,4R,5R)-6'-chloro-5-(3-chlorophenyl)-1,1',2,2',3,5,6,7-octahydro-3-(2-methylphenyl)-spiro[4H-azepine-4,3'-[3H]-indole]-2',7-dione and (3S,4R,5R)-6'-chloro-3-(3-chlorophenyl)-1,1',2,2',3,5,6,7-octahydro-5-(2-methylphenyl)-spiro[4H-azepine-4,3'-[3H]-indole]-2',7-dione

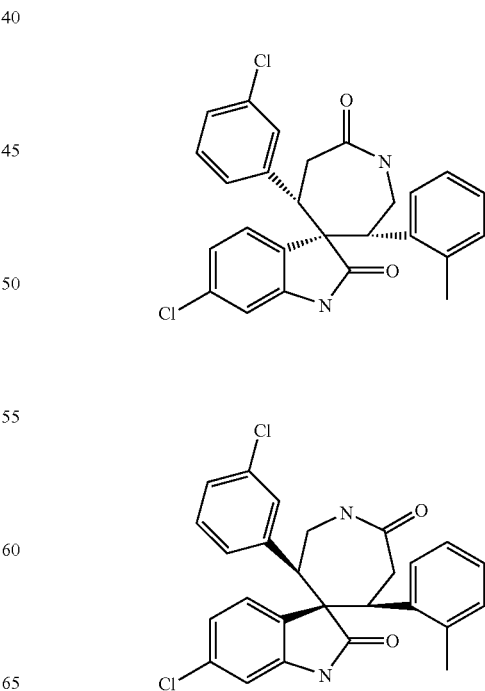

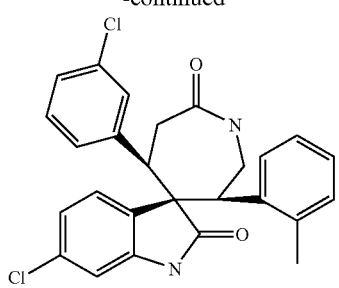

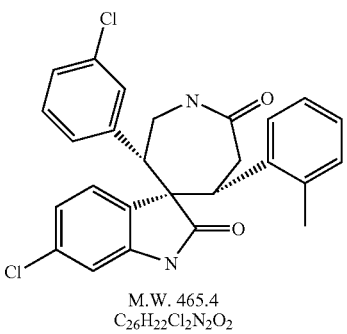

M.W. 465.4
$C_{26}H_{22}Cl_2N_2O_2$

In a manner similar to the method described in example 2 (method A), rac-(1S,2S,6R)-6'-chloro-2-(3-chlorophenyl)-6-(2-methylphenyl)spiro[cyclohexane-1,3'-[3H]indole]-2',4 (1'H)-dione (115.0 mg, 0.26 mmole) was reacted with NaN3 (42.3 mg, 0.65 mmole) in the presence of TiCl4 (1.0 M in CH$_2$Cl$_2$, 0.26 mL) (Aldrich) in acetonitrile (10 mL) followed by chiral chromatograph to give (3R,4S,5S)-6'-chloro-5-(3-chlorophenyl)-1,1',2,2',3,5,6,7-octahydro-3-(2-methylphenyl)-spiro[4H-azepine-4,3'-[3H]-indole]-2',7-dione (11.0 mg): HRMS (ES$^+$) m/z Calcd for $C_{26}H_{22}Cl_2N_2O_2$+H [(M+H)$^+$]: 465.1131. Found: 465.1131; (3R,4S,5S)-6'-chloro-3-(3-chlorophenyl)-1,1',2,2',3,5,6,7-octahydro-5-(2-methylphenyl)-spiro[4H-azepine-4,3'-[3H]-indole]-2',7-dione (10.6 mg); HRMS (ES$^+$) m/z Calcd for $C_{26}H_{22}Cl_2N_2O_2$+H [(M+H)$^+$]: 465.1131. Found: 465.1130.

(3S,4R,5R)-6'-chloro-5-(3-chlorophenyl)-1,1',2,2',3,5,6,7-octahydro-3-(2-methylphenyl)-spiro[4H-azepine-4,3'-[3H]-indole]-2',7-dione (10.1 mg): HRMS (ES$^+$) m/z Calcd for $C_{26}H_{22}Cl_2N_2O_2$+H [(M+H)$^+$]: 465.1131. Found: 465.1131.

(3S,4R,5R)-6'-chloro-3-(3-chlorophenyl)-1,1',2,2',3,5,6,7-octahydro-5-(2-methylphenyl)-spiro[4H-azepine-4,3'-[3H]-indole]-2',7-dione (10.2 mg): HRMS (ES$^+$) m/z Calcd for $C_{26}H_{22}Cl_2N_2O_2$+H [(M+H)$^+$]: 465.1131. Found: 465.1131.

Example 11

Preparation of Rac-(1R,2S,6S)-6'-chloro-2-(3-chlorophenyl)-6-(2-methylpropyl)-spiro[cyclohexane-1,3'-[3H]indole]-2',4(1'H)-dione (scheme 2)

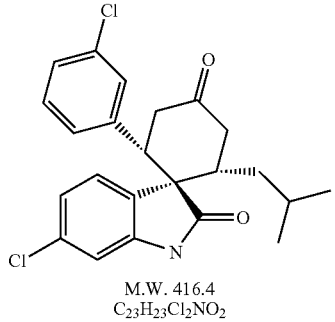

M.W. 416.4
$C_{23}H_{23}Cl_2NO_2$

In a flask equipped with septum and stirring bar, a mixture of CuCl (49.0 mg, 0.50 mmol) and Ph$_3$P (181.1 mg, 0.50 mmol) was suspended in THF (10 mL). After stirring under argon at rt for 30 min, rac-(1R,2S)-6'-chloro-2-(3-chlorophenyl)spiro[5-cyclohexene-1,3'-[3H]indole]-2',4(1'H)-dione (179 mg, 0.50 mmol) was added in one portion. After additional stirring for 10 min, 2-methylpropylmagnesium bromide (2.0 M in ether, 1.25 mL, 2.5 mmol) was added dropwise to the resulting mixture during 5 min at 0° C. The reaction mixture was allowed to stir under argon at 0° C. to −10° C. for 2.5 h. Sat.NH4Cl was then added to quech the reaction. The organic phase was separated. TLC/MS (AcOEt/Hex=½) showed mixture of two isomers of the desired products and no SM. The mixture was then separated by flash column to give rac-(1R,2S,6S)-6'-chloro-2-(3-chlorophenyl)-6-(2-methylpropyl)-spiro[cyclohexane-1,3'-[3H]indole]-2',4(1'H)-dione (165.1 mg, 80.3%): HRMS (ES$^+$) m/z Calcd for $C_{23}H_{23}Cl_2NO_2$+H [(M+H)$^+$]: 416.1179, Found: 416.1179.

Example 12

Preparation of (3R,4S,5R)-6'-chloro-3-(3-chlorophenyl)-1,1',2,2',3,5,6,7-octahydro-5(2-methylpropyl)-spiro[4H-azepine-4,3'-[3H]-indole]-2',7-dione, (3R,4S,5R)-6'-chloro-5-(3-chlorophenyl)-1,1',2,2',3,5,6,7-octahydro-3-(2-methylpropyl)-spiro[4H-azepine-4,3'-[3H]-indole]-2',7-dione, (3S,4R,5S)-6'-chloro-3-(3-chlorophenyl)-1,1',2,2',3,5,6,7-octahydro-5-(2-methylpropyl)-spiro[4H-azepine-4,3'-[3H]-indole]-2',7-dione, and (3S,4R,5S)-6'-chloro-5-(3-chlorophenyl)-1,1',2,2',3,5,6,7-octahydro-3-(2-methylpropyl)-spiro[4H-azepine-4,3'-[3H]-indole]-2',7-dione.

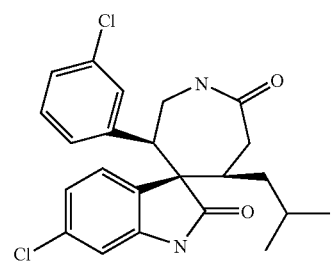

-continued

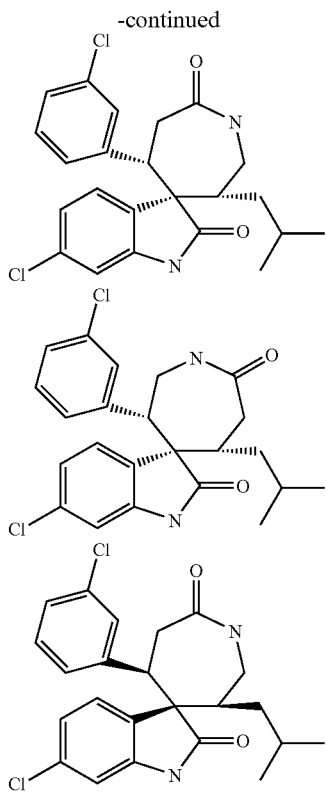

M. W. 431.4 C$_{23}$H$_{24}$Cl$_2$N$_2$O$_2$

Step 1

A suspension of rac-(1R,2S,6S)-6'-chloro-2-(3-chlorophenyl)-6-(2-methylpropyl)-spiro[cyclohexane-1,3'-[3H]indole]-2',4(1'H)-dione (135.0 mg, 0.32 mmol), NaOH (100.0 mg, 2.5 mmole) and NH$_2$OH—HCl (173.8 mg, 2.5 mmol) in EtOH-water (3/2, 5 mL) was allowed to reflux for 3 hrs. The reaction was cooled to room temperature, and water was added. The mixture was extracted with ethyl acetate. The organic layer was separated, dried over MgSO$_4$, and concentrated. The residue was purified by chromatography to give the corresponding oxime (136.2 mg, 97.4%) as a white solid which was used in the next step without further purification.

Step 2

To the solution of rac-E/Z-spiro[cyclohexane-1,3'-[3H]indole]-2',4(1'H)-dione-4-oxime obtained above (130.0 mg, 0.30 mmol) and DMAP (80.5 mg, 0.66 mmol) in dichloromethane (2 mL) was added a solution of p-toluenesulfonyl chloride (125.9 mg, 0.66 mmol) in dichloromethane (1 mL) at room temperature. The reaction mixture was stirred at room temperature for 1 h. The reaction was then concentrated and the residue was purified by chromatography to give the corresponding E and Z isomers of the spiro[cyclohexane-1,3'-[3H]indole]-2',4(1'H)-dione-4-(O-p-toulenesulfonyl)-oximes (135.9 mg, 77.3%) as a white solid, which was used in the next step without further purification.

Step 3

Rac-Z-or-E-spiro[cyclohexane-1,3'-[3H]indole]-2',4(1'H)-dione-4-(O-p-toulenesulfonyl)-oxime (120.0 mg, 0.21 mmol) prepared in step 2 was dissolved in THF/H$_2$O (3/1.5 mL) and heated in a sealed tube under microwave irradiation at 100° C. for 20 min. After diluted with AcOEt the mixture was washed with water, dried over Na$_2$SO$_4$ and concentrated. The residue was purified by chiral column chromatography to give (3R,4S,5R)-4'-chloro-3-(3-chlorophenyl)-1,1',2,2',3,5,6,7-octahydro-5-(2-methylpropyl)-spiro[4H-azepine-4,3'-[3H]-indole]-2',7-dione (13.8 mg): HRMS (ES$^+$) m/z Calcd for C$_{23}$H$_{24}$Cl$_2$N$_2$O$_2$+H [(M+H)$^+$]: 431.1288. Found: 431.1287; (3R,4S,5R)-6'-chloro-5-(3-chlorophenyl)-1,1',2,2',3,5,6,7-octahydro-3-(2-methylpropyl)-spiro[4H-azepine-4,3'-[3H]-indole]-2',7-dione (15.1 mg): HRMS (ES$^+$) m/z Calcd for C$_{23}$H$_{24}$Cl$_2$N$_2$O$_2$+H [(M+H)$^+$]: 431.1288. Found: 431.1287; (3S,4R,5S)-6'-chloro-3-(3-chlorophenyl)-1,1',2,2',3,5,6,7-octahydro-5-(2-methylpropyl)-spiro[4H-azepine-4,3'-[3H]-indole]-2',7-dione (14.1 mg): HRMS (ES$^+$) m/z Calcd for C$_{23}$H$_{24}$Cl$_2$N$_2$O$_2$+H [(M+H)$^+$]: 431.1288. Found: 431.1287; (3S,4R,5S)-4'-chloro-5-(3-chlorophenyl)-1,1',2,2',3,5,6,7-octahydro-3-(2-methylpropyl)-spiro[4H-azepine-4,3'-[3H]-indole]-2',7-dione (15.2 mg): HRMS (ES$^+$) m/z Calcd for C$_{23}$H$_{24}$Cl$_2$N$_2$O$_2$+H [(M+H)$^+$]: 431.1288. Found: 431.1288.

Example 13

Preparation of (3R,4S,5S)-6'-chloro-3-(3-chlorophenyl)-5-cyclopropyl-1,1',2,2',3,5,6,7-octahydrospiro[4H-azepine-4,3'-[3H]-indole]-2',7-dione, (3R,4S,5S)-6'-chloro-5-(3-chlorophenyl)-3-cyclopropyl-1,1',2,2',3,5,6,7-octahydrospiro[4H-azepine-4,3'-[3H]-indole]-2',7-dione, (3S,4R,5R)-6'-chloro-3-(3-chlorophenyl)-5-cyclopropyl-1,1',2,2',3,5,6,7-octahydrospiro[4H-azepine-4,3'-[3H]-indole]-2',7-dione and (3S,4R,5R)-6'-chloro-5-(3-chlorophenyl)-3-cyclopropyl-1,1',2,2',3,5,6,7-octahydrospiro[4H-azepine-4,3'-[3H]-indole]-2',7-dione.

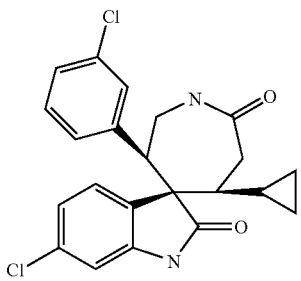

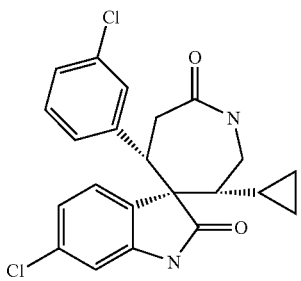

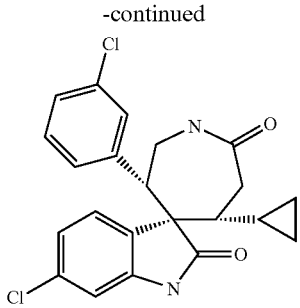

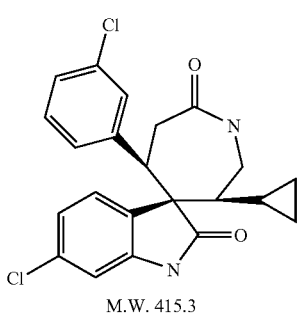

M.W. 415.3
$C_{22}H_{20}Cl_2N_2O_2$

In a manner similar to the method described in example 2 (method B), rac-(1R,2S,6R)-6'-chloro-2-(3-chlorophenyl)-6-cyclopropylspiro[cyclohexane-1,3'-[3H]indole]-2',4(1'H)-dione (148.1 mg, 0.37 mmole) was reacted with $NH_2OH$—HCl (128.6 mg, 1.85 mmol), NaOH (74.0 mg, 1.85 mmole) in EtOH-water (3/2, 10 mL) at refluxing for 2 hrs, followed by reacting with p-toluenesulfonyl chloride (141.1 mg, 0.74 mmol) in dichloromethane (1 mL) at room temperature for 30 min, and heating under microwave irradiation at 90° C. for 20 min. After diluted with AcOEt the mixture was washed with water, dried over $Na_2SO_4$ and concentrated. The residue was purified by chiral column chromatography to give (3R,4S,5S)-6'-chloro-3-(3-chlorophenyl)-5-cyclopropyl-1,1',2,2',3,5,6,7-octahydrospiro[4H-azepine-4,3'-[3H]-indole]-2',7-dione (22.5 mg): HRMS (ES$^+$) m/z Calcd for $C_{22}H_{20}Cl_2N_2O_2$+H [(M+H)$^+$]: 415.0975, Found: 415.0974; (3R,4S,5S)-6'-chloro-5-(3-chlorophenyl)-3-cyclopropyl-1,1',2,2',3,5,6,7-octahydrospiro[4H-azepine-4,3'-[3H]-indole]-2',7-dione (25.8 mg): HRMS (ES$^+$) m/z Calcd for $C_{22}H_{20}Cl_2N_2O_2$+H [(M+H)$^+$]: 415.0975, Found: 415.0974; (3S,4R,5R)-6'-chloro-3-(3-chlorophenyl)-5-cyclopropyl-1,1',2,2',3,5,6,7-octahydrospiro[4H-azepine-4,3'-[3H]-indole]-2',7-dione (14.1 mg): HRMS (ES$^+$) m/z Calcd for $C_{22}H_{20}Cl_2N_2O_2$+H [(M+H)$^+$]: 415.0975, Found: 415.0975; and (3S,4R,5R)-6'-chloro-5-(3-chlorophenyl)-3-cyclopropyl-1,1',2,2',3,5,6,7-octahydrospiro[4H-azepine-4,3'-[3H]-indole]-2',7-dione (15.2 mg): HRMS (ES$^+$) m/z Calcd for $C_{22}H_{20}Cl_2N_2O_2$+H [(M+H)$^+$]: 415.0975, Found: 415.0975.

Example 14

Preparation of (3R,4S,5S)-4'-chloro-3-(3-chlorophenyl)-1,1',2,2',3,5,6,7-octahydro-5-(1-methylethyl)-spiro[4H-azepine-4,3'-[3H]-indole]-2',7-dione, (3R,4S,5R)-6'-chloro-5-(3-chlorophenyl)-1,1',2,2',3,5,6,7-octahydro-3-(1-methylethyl)-spiro[4H-azepine-4,3'-[3H]-indole]-2',7-dione, (3S,4R,5R)-6'-chloro-3-(3-chlorophenyl)-1,1',2,2',3,5,6,7-octahydro-5-(1-methylethyl)-spiro[4H-azepine-4,3'-[3H]-indole]-2',7-dione, (3S,4R,5S)-6'-chloro-5-(3-chlorophenyl)-1,1',2,2',3,5,6,7-octahydro-3-(1-methylethyl)-spiro[4H-azepine-4,3'-[3H]-indole]-2',7-dione.

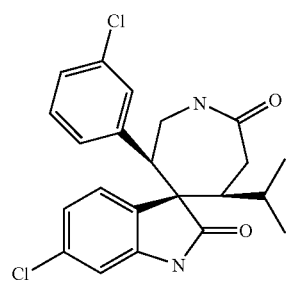

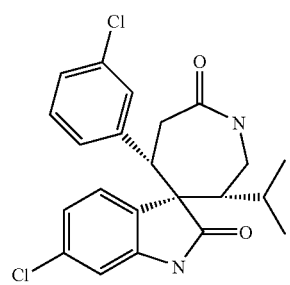

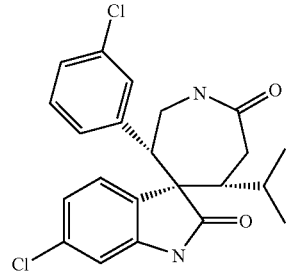

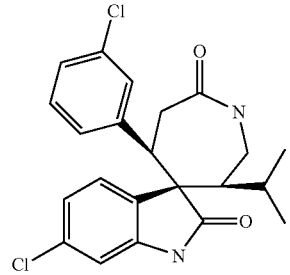

M.W. 417.3
$C_{22}H_{22}Cl_2N_2O_2$

In a manner similar to the method described in example 2 (method B), rac-(1R,2S,6R)-6'-chloro-2-(3-chlorophenyl)-6-(1-methylethyl)-spiro[cyclohexane-1,3'-[3H]indole]-2',4

(1'H)-dione (402.3 mg, 1.00 mmole) was reacted with NH$_2$OH—HCl (347.5 mg, 5.00 mmol), NaOH (200.0 mg, 5.00 mmole) in EtOH-water (3/2, 15 mL) at refluxing for 3 hrs, followed by reacting with p-toluenesulfonyl chloride (762.8 mg, 4.00 mmol) in dichloromethane (20 mL) at room temperature for 2 hrs, and heating under microwave irradiation at 100° C. for 20 min. After diluted with AcOEt the mixture was washed with water, dried over Na$_2$SO$_4$ and concentrated. The residue was purified by chiral column chromatography to give (3R,4S,5S)-6'-chloro-3-(3-chlorophenyl)-1,1',2,2',3,5,6,7-octahydro-5-(1-methylethyl)-spiro[4H-azepine-4,3'-[3H]-indole]-2',7-dione (18.9 mg): HRMS (ES$^+$) m/z Calcd for C$_{22}$H$_{22}$Cl$_2$N$_2$O$_2$+H [(M+H)$^+$]: 417.1131. Found: 417.1132; (3R,4S,5R)-6'-chloro-5-(3-chlorophenyl)-1,1',2,2',3,5,6,7-octahydro-3-(1-methylethyl)-spiro[4H-azepine-4,3'-[3H]-indole]-2',7-dione (18.2 mg): HRMS (ES$^+$) m/z Calcd for C$_{22}$H$_{22}$Cl$_2$N$_2$O$_2$+H [(M+H)$^+$]: 417.1131. Found: 417.1132; (3S,4R,5R)-6'-chloro-3-(3-chlorophenyl)-1,1',2,2',3,5,6,7-octahydro-5-(1-methylethyl)-spiro[4H-azepine-4,3'-[3H]-indole]-2',7-dione (17.6 mg): HRMS (ES$^+$) m/z Calcd for C$_{22}$H$_{22}$Cl$_2$N$_2$O$_2$+H [(M+H)$^+$]: 417.1131. Found: 417.1132; and (3S,4R,5S)-6'-chloro-5-(3-chlorophenyl)-1,1',2,2',3,5,6,7-octahydro-3-(1-methylethyl)-spiro[4H-azepine-4,3'-[3H]-indole]-2',7-dione (15.1 mg): HRMS (ES$^+$) m/z Calcd for C$_{22}$H$_{22}$Cl$_2$N$_2$O$_2$+H [(M+H)$^+$]: 417.1131, Found: 417.1132.

Example 15

Preparation of (3R,4S,5S)-6'-chloro-3-(3-chlorophenyl)-5-(5-fluoro-2-methylphenyl)-1,1',2,2',3,5,6,7-octahydrospiro[4H-azepine-4,3'-[3H]-indole]-2',7-dione, (3R,4S,5S)-6'-chloro-5-(3-chlorophenyl)-3-(5-fluoro-2-methylphenyl)-1,1',2,2',3,5,6,7-octahydrospiro[4H-azepine-4,3'-[3H]-indole]-2',7-dione, (3S,4R,5R)-6'-chloro-3-(3-chlorophenyl)-5-(5-fluoro-2-methylphenyl)-1,1',2,2',3,5,6,7-octahydrospiro[4H-azepine-4,3'-[3H]-indole]-2',7-dione (3S,4R,5R)-6'-chloro-5-(3-chlorophenyl)-3-(5-fluoro-2-methylphenyl)-1,1',2,2',3,5,6,7-octahydrospiro[4H-azepine-4,3'-[3H]-indole]-2',7-dione.

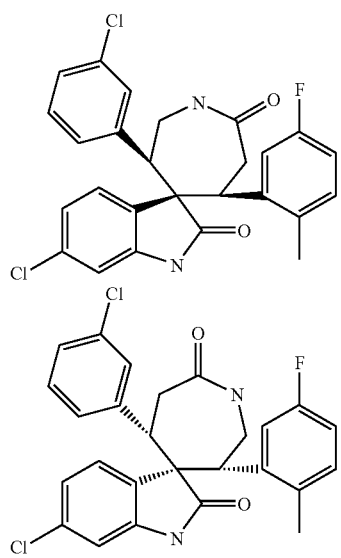

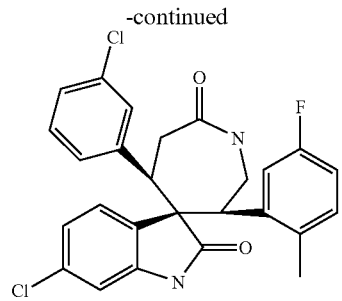

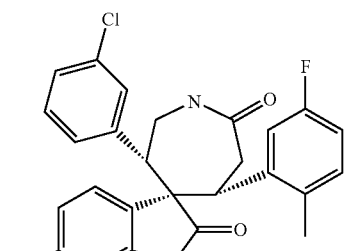

M.W. 483.4
C$_{26}$H$_{21}$Cl$_2$FN$_2$O$_2$

In a manner similar to the method described in example 2 (method B), rac-(1S,2S,6R)-6'-chloro-2-(3-chlorophenyl)-6-(5-fluoro-2-methylphenyl)-spiro[cyclohexane-1,3'-[3H]indole]-2',4(1'H)-dione (130.0 mg, 0.28 mmole) was reacted with NH$_2$OH—HCl (97.3 mg, 1.40 mmol), NaOH (56.0 mg, 1.40 mmole) in EtOH-water (3/2, 5 mL) at refluxing for 3 hrs, followed by reacting with p-toluenesulfonyl chloride (114.4 mg, 0.60 mmol) in dichloromethane (10 mL) at room temperature for 2 hrs, and heating under microwave irradiation at 100° C. for 20 min. After diluted with AcOEt the mixture was washed with water, dried over Na$_2$SO$_4$ and concentrated. The residue was purified by chiral column chromatography to give (3R,4S,5S)-6'-chloro-3-(3-chlorophenyl)-5-(5-fluoro-2-methylphenyl)-1,1',2,2',3,5,6,7-octahydrospiro[4H-azepine-4,3'-[3H]-indole]-2',7-dione (15.9 mg): HRMS (ES$^+$) m/z Calcd for C$_{26}$H$_{21}$Cl$_2$FN$_2$O$_2$+H [(M+H)$^+$]: 483.1037, Found: 483.1036; (3R,4S,5S)-6'-chloro-5-(3-chlorophenyl)-3-(5-fluoro-2-methylphenyl)-1,1',2,2',3,5,6,7-octahydrospiro[4H-azepine-4,3'-[3H]-indole]-2',7-dione (11.3 mg): HRMS (ES$^+$) m/z Calcd for C$_{26}$H$_{21}$Cl$_2$FN$_2$O$_2$+H [(M+H)$^+$]: 483.1037, Found: 483.1037; (3S,4R,5R)-6'-chloro-5-(3-chlorophenyl)-3-(5-fluoro-2-methylphenyl)-1,1',2,2',3,5,6,7-octahydrospiro[4H-azepine-4,3'-[3H]-indole]-2',7-dione (8.3 mg): HRMS (ES$^+$) m/z Calcd for C$_{26}$H$_{21}$Cl$_2$FN$_2$O$_2$+H [(M+H)$^+$]: 483.1037, Found: 483.1036; (3S,4R,5R)-6'-chloro-3-(3-chlorophenyl)-5-(5-fluoro-2-methylphenyl)-1,1',2,2',3,5,6,7-octahydrospiro[4H-azepine-4,3'-[3H]-indole]-2',7-dione (12.5 mg): HRMS (ES$^+$) m/z Calcd for C$_{26}$H$_{21}$Cl$_2$FN$_2$O$_2$+H [(M+H)$^+$]: 483.1037, Found: 483.1038.

Example 16

Preparation of (3R,4S,5S)-6'-chloro-3-(3-chlorophenyl)-1,1',2,2',3,5,6,7-octahydro-5-phenyl-spiro[4H-azepine-4,3'-[3H]-indole]-2',7-dione, (3R,4S,5S)-6'-chloro-5-(3-chlorophenyl)-1,1',2,2',3,5,6,7-octahydro-3-phenyl-spiro[4H-azepine-4,3'-[3H]-indole]-2',7-dione, (3S,4R,5R)-6'-chloro-3-(3-chlorophenyl)-1,1',2,2',3,5,6,7-octahydro-3-phenyl-spiro[4H-azepine-4,3'-[3H]-indole]-2',7-dione, (3S,4R,5R)-6'-chloro-5-(3-chlorophenyl)-1,1',2,2',3,5,6,7-octahydro-3-phenyl-spiro[4H-azepine-4,3'-[3H]-indole]-2',7-dione.

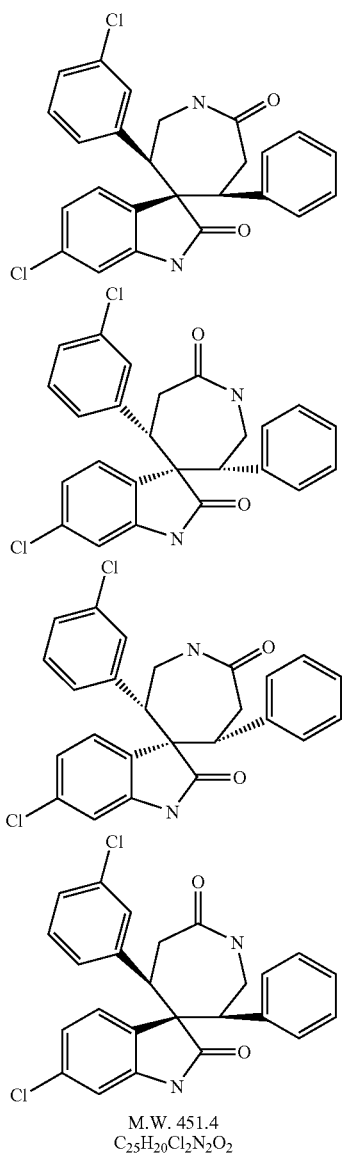

M.W. 451.4
$C_{25}H_{20}Cl_2N_2O_2$

In a manner similar to the method described in example 2 (method B), rac-(1R,2S,6R)-6'-chloro-2-(3-chlorophenyl)-6-phenylspiro[cyclohexane-1,3'-[3H]indole]-2',4(1'H)-dione (150.0 mg, 0.34 mmole) was reacted with $NH_2OH$—HCl (119.5 mg, 1.72 mmol), NaOH (68.8 mg, 1.72 mmole) in EtOH-water (3/2, 10 mL) at refluxing for 2 hrs, followed by reacting with p-toluenesulfonyl chloride (133.1 mg, 0.70 mmol) in dichloromethane (10 mL) at room temperature for 2 hrs, and heating under microwave irradiation at 90° C. for 20 min. After diluted with AcOEt the mixture was washed with water, dried over $Na_2SO_4$ and concentrated. The residue was purified by chiral column chromatography to give (3R,4S,5S)-6'-chloro-3-(3-chlorophenyl)-1,1',2,2',3,5,6,7-octahydro-5-phenyl-spiro[4H-azepine-4,3'-[3H]-indole]-2',7-dione (19.4 mg): HRMS (ES$^+$) m/z Calcd for $C_{25}H_{20}Cl_2N_2O_2$+H [(M+H)$^+$]: 451.0975, Found: 451.0974; (3R,4S,5S)-6'-chloro-5-(3-chlorophenyl)-1,1',2,2',3,5,6,7-octahydro-3-phenyl-spiro[4H-azepine-4,3'-[3H]-indole]-2',7-dione (20.1 mg): HRMS (ES$^+$) m/z Calcd for $C_{25}H_{20}Cl_2N_2O_2$+H [(M+H)$^+$]: 451.0975, Found: 451.0974; (3S,4R,5R)-6'-chloro-3-(3-chlorophenyl)-1,1',2,2',3,5,6,7-octahydro-3-phenyl-spiro[4H-azepine-4,3'-[3H]-indole]-2',7-dione (20.5 mg): HRMS (ES$^+$) m/z Calcd for $C_{25}H_{20}Cl_2N_2O_2$+H [(M+H)$^+$]: 451.0975. Found: 451.0974; (3S,4R,5R)-6'-chloro-5-(3-chlorophenyl)-1,1',2,2',3,5,6,7-octahydro-3-phenyl-spiro[4H-azepine-4,3'-[3H]-indole]-2',7-dione (21.6 mg): HRMS (ES$^+$) m/z Calcd for $C_{25}H_{20}Cl_2N_2O_2$+H [(M+H)$^+$]: 451.0975. Found: 451.0974.

Example 17

Preparation of rac-(3S,4R,5S)-6'-bromo-3-(3-chlorophenyl)-1,1',2,2',3,5,6,7-octahydro-5-methoxy-spiro[4H-azepine-4,3'-[3H]-indole]-2',7-dione, rac-(3R,4R,5S)-6'-bromo-5-(3-chlorophenyl)-1,1',2,2',3,5,6,7-octahydro-3-methoxy-spiro[4H-azepine-4,3'-[3H]-indole]-2',7-dione

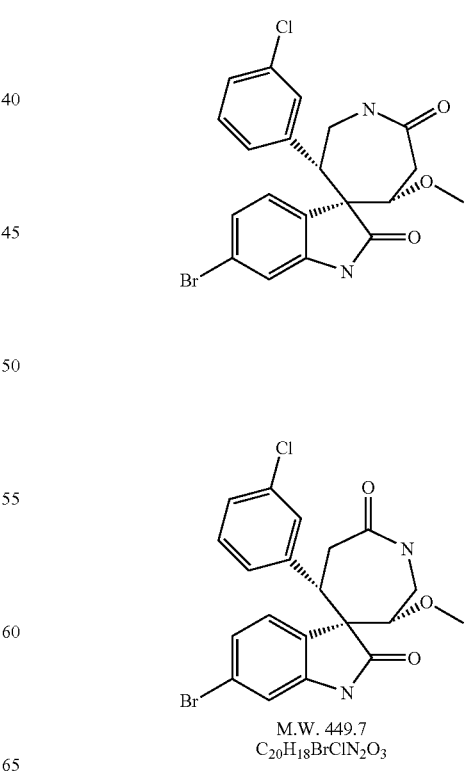

M.W. 449.7
$C_{20}H_{18}BrClN_2O_3$

Step 1

Preparation of Intermediate E/Z-6-bromo-3-(3-chloro-benzylidene)-1,3-dihydro-indol-2-one

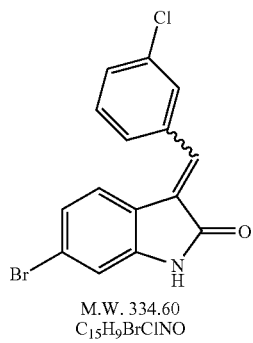

M.W. 334.60
C$_{15}$H$_9$BrClNO

To the mixture of 6-bromooxindole (5 g, 23.6 mmol) (Combi-blocks) and 3-chloro-benzaldehyde (3.3 g, 23.6 mmol) (Aldrich) in methanol (50 mL) was added pyrrolidine (1.7 g, 23.6 mmol) (Aldrich) dropwise. The mixture was then heated at 90° C. for 4 h. After cooled to 0° C., the mixture was filtered and resulting precipitate was collected, dried to give a mixture of E/Z-6-bromo-3-(3-chloro-benzylidene)-1,3-dihydro-indol-2-one as a bright yellow solid (Yield 5 g, 63%).

Step 2

Preparation of Rac-(1R,2R)-6'-bromo-2-(3-chlorophenyl)spiro[5-cyclohexene-1,3'-[3H]indole]-2',4(1'H)-dione, Rac-(1R,2S)-6'-bromo-2-(3-chlorophenyl)spiro[5-cyclohexene-1,3'-[3H]indole]-2',4(1'H)-dione, and Rac-(1R,2S,6S)-6'-bromo-2-(3-chlorophenyl)-6-methoxyspiro[cyclohexane-1,3'-[3H]indole]-2',4(1'H)-dione

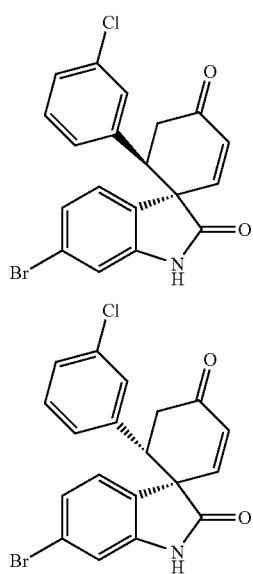

-continued

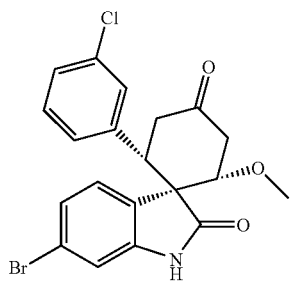

To a suspension of E/Z-6-bromo-3-(3-chloro-benzylidene)-1,3-dihydro-indol-2-one (4.3 g, 12.9 mmol) in toluene (50 mL) in a sealed tube was added (3-methoxy-1-methylene-allyloxy)-trimethyl-silane (5 g, 29 mmol). The reaction mixture was allowed to stir at 150° C. for 24 h. The solvent was removed by concentration. The residue was dissolved in MeOH (80 mL) and treated with 1 N NaOH (20 mL) at room temperature for 2 h. The reaction mixture was then diluted with AcOEt and washed with water and brine. After concentration the residue was purified by flash column (11%-25% AcOEt in Hex) to give rac-(1R,2R)-6'-bromo-2-(3-chlorophenyl)-spiro[5-cyclohexene-1,3'-[3H]indole]-2',4(1'H)-dione (0.4 g, 7.7%) as a white solid. HRMS (ES$^+$) m/z Calcd for C$_{19}$H$_{13}$BrClNO$_2$+H [(M+H)$^+$]: 401.9891. Found: 401.9891; rac-(1R,2S)-6'-bromo-2-(3-chlorophenyl)spiro[5-cyclohexene-1,3'-[3H]indole]-2',4(1'H)-dione (1.2 g, 23%) as a white solid. HRMS (ES$^+$) m/z Calcd for C$_{19}$H$_{13}$BrClNO$_2$+H [(M+H)$^+$]: 401.9891. Found: 401.9891; and rac-(1R,2S,6S)-6'-bromo-2-(3-chlorophenyl)-6-methoxyspiro[cyclohexane-1,3'-[3H]indole]-2',4(1'H)-dione (2.1 g, 39.8%) as a off white solid.

HRMS (ES$^+$) m/z Calcd for C$_{20}$H$_{17}$BrClNO$_3$+H [(M+H)$^+$]: 434.0153, Found: 434.0153.

Step 3

Preparation of Rac-E-(1S,2S,6S)-6'-bromo-2-(3-chlorophenyl)-6-methoxy-spiro[cyclohexane-1,3'-[3H]indole]-2',4(1'H)-dione-4-oxime and Rac-Z-(1S,2S,6S)-6'-bromo-2-(3-chlorophenyl)-6-methoxy-spiro[cyclohexane-1,3'-[3H]indole]-2',4(1'H)-dione-4-oxime

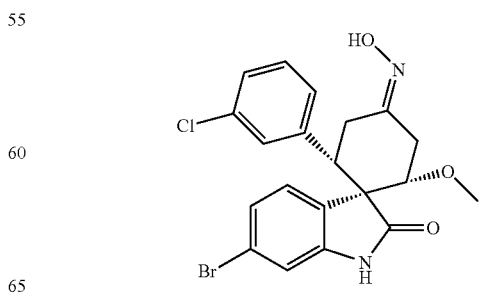

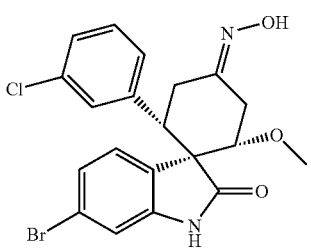

To the suspension of rac-(1R,2S,6S)-6'-bromo-2-(3-chlorophenyl)-6-methoxyspiro[cyclohexane-1,3'-[3H]indole]-2',4(1'H)-dione (1.69 g, 3.89 mmol) and NH₄OH—HCl (0.27 g, 3.89 mmol) in EtOH (40 mL) was added a queous NaOH solution (1N, 4 mL, 4 mmol). The reaction mixture was heated at reflux for 1 h. TLC analysis indicated the formation of desired product and complete consumption of starting material. The reaction was cooled to room temperature, and water was added. The mixture was extracted with ethyl acetate. The organic layer was separated, dried over MgSO₄, and concentrated. The residue was purified by chromatography (EtOAc:hexanes=1:3, 1:2, then 1:1) to give the less polar product rac-E-(1R,2S,6S)-6'-bromo-2-(3-chlorophenyl)-6-methoxy spiro[cyclohexane-1,3'-[3H]indole]-2',4(1'H)-dione-4-oxime as a white solid (0.8 g, 46%): HRMS (ES⁺) m/z Calcd for $C_{22}H_{18}BrClN_2O_3$+H [(M+H)⁺]: 449.0262, Found: 449.0260; rac-Z-(1R,2S,6S)-6'-bromo-2-(3-chlorophenyl)-6-methoxy spiro[cyclohexane-1,3'-[3H]indole]-2',4(1'H)-dione-4-oxime as a white solid (0.8 g, 46%): HRMS (ES⁺) m/z Calcd for $C_{22}H_{18}BrClN_2O_3$+H [(M+H)⁺]: 449.0262, Found: 449.0261.

Step 4

Preparation of Rac-E-(1R,2S,6S)-6'-bromo-2-(3-chlorophenyl)-6-methoxyl-spiro[cyclohexane-1,3'-[3H]indole]-2',4(1'H)-dione-4-(O-p-toulenesulfonyl)-oxime and Rac-Z-(1R,2S,6S)-6'-bromo-2-(3-chlorophenyl)-6-methoxyl-spiro[cyclohexane-1,3'-[3H]indole]-2',4(1'H)-dione-4-(O-p-toulenesulfonyl)-oxime

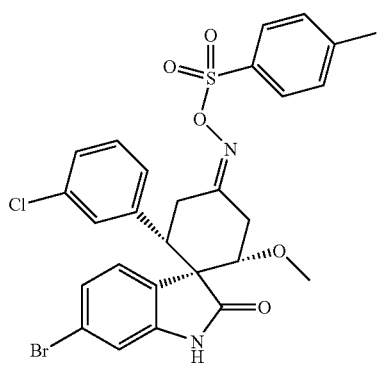

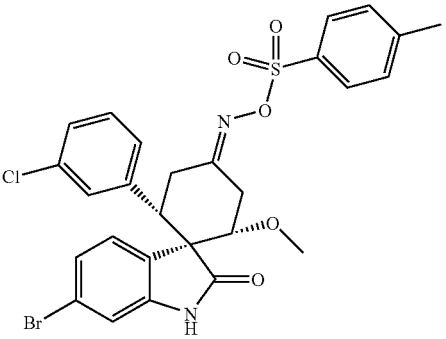

To the solution of rac-E-(1R,2S,6S)-6'-bromo-2-(3-chlorophenyl)-6-methoxy spiro[cyclohexane-1,3'-[3H]indole]-2',4(1'H)-dione-4-oxime (0.7 g, 1.56 mmol) and DMAP (0.19 g, 1.56 mmol) in dichloromethane (35 mL) was added a solution of p-toluenesulfonyl chloride (0.3 g, 1.56 mmol) in dichloromethane (20 mL) at room temperature. The reaction mixture was stirred at room temperature for 1 h. The mixture was then concentrated and the residue was purified by chromatography (20%-40% AcOEt in hexanes) to give Rac-E-(1R,2S,6S)-6'-bromo-2-(3-chlorophenyl)-6-methoxy spiro[cyclohexane-1,3'-[3H]indole]-2',4(1'H)-dione-4-(O-p-toulenesulfonyl-oxime) as a white solid (0.72 g, 77%):
HRMS (ES⁺) m/z Calcd for $C_{27}H_{24}BrClSN_2O_5$+H [(M+H)⁺]: 603.0351, Found: 603.0352.

To the solution of rac-Z-(1R,2S,6S)-6'-bromo-2-(3-chlorophenyl)-6-methoxy spiro[cyclohexane-1,3'-[3H]indole]-2',4(1'H)-dione-4-oxime (0.67 g, 1.49 mmol) and DMAP (0.18 g, 1.49 mmol) in dichloromethane (30 mL) was added a solution of p-toluenesulfonyl chloride (0.28 g, 1.49 mmol) in dichloromethane (20 mL) at room temperature. The reaction mixture was stirred at room temperature for 1 h. The mixture was then concentrated and the residue was purified by chromatography (20%-40% AcOEt in hexanes) to give Rac-E-(1R,2S,6S)-6'-bromo-2-(3-chlorophenyl)-6-methoxy spiro[cyclohexane-1,3'-[3H]indole]-2',4(1'H)-dione-4-(O-p-toulenesulfonyl)-oxime as a white solid (0.7 g, 78%):
HRMS (ES⁺) m/z Calcd for $C_{27}H_{24}BrClSN_2O_5$+H [(M+H)⁺]: 603.0351, Found: 603.0351.

Step 5

Preparation of Rac-(3'S,3S,5'S)-6-bromo-3'-(3-chlorophenyl)-5'-methoxy spiro[3H-indole-3,4'-azopane]-2,7'(1'H)-dione and Rac-(3'R,3S,5'S)-6-bromo-5'-(3-chlorophenyl)-3'-methoxy spiro[3H-indole-3,4'-azopane]-2,7'(1'H)-dione Rac-Z-(1R,2S,6S)-6'-bromo-2-(3-chlorophenyl)-6-methoxy spiro[cyclohexane-1,3'-[3H]indole]-2',4(1'H)-dione-4-(O-p-toulenesulfonyl)-oxime (0.6 g, 1 mmol) prepared in step 4 was dissolved in THF/H₂O (10/5 mL) and heated in a sealed tube under microwave irradiation at 100° C. for 30 min. After diluted with AcOEt the mixture was washed with water, dried over Na₂SO₄ and concentrated. The residue was purified by chromatography (5% MeOH in EtOAc) to give rac-(3'S,3S,5'S)-6-bromo-3'-(3-chlorophenyl)-5'-methoxy spiro[3H-indole-3,4'-azopane]-2,7'(1'H)-dione as a white solid (0.25 g, 56%): HRMS (ES⁺) m/z Calcd for $C_{20}H_{18}BrClN_2O_3$+H [(M+H)⁺]: 449.0262, Found: 449.0261.
Rac-E-(1R,2S,6S)-6'-bromo-2-(3-chlorophenyl)-6-methoxy spiro[cyclohexane-1,3'-[3H]indole]-2',4(1'H)-dione-4-

(O-p-toulenesulfonyl)-oxime (0.4 g, 0.66 mmol) prepared in step 4 was dissolved in THF/H$_2$O (10/5 mL) and heated in a sealed tube under microwave irradiation at 100° C. for 30 min. After diluted with AcOEt the mixture was washed with water, dried over Na$_2$SO$_4$ and concentrated. The residue was purified by chromatography (5% MeOH in EtOAc) to give rac-(3'R,3S,5'S)-6-bromo-5'-(3-chlorophenyl)-3'-methoxy spiro[3H-indole-3,4'-azopane]-2,7'(1'H)-dione as a white solid (0.15 g, 51%): HRMS (ES$^+$) m/z Calcd for C$_{20}$H$_{18}$BrClN$_2$O$_3$+H [(M+H)$^+$]: 449.0262, Found: 449.0262.

Example 18

Preparation of (3S,4R,5R)-6'-bromo-5-(3-chlorophenyl)-1,1',2,2',3,5,6,7-octahydro-3-(1-methylethenyl)-spiro[4H-azepine-4,3'-[3H]-indole]-2',7-dione, (3R,4S,5S)-6'-bromo-5-(3-chlorophenyl))-1,1',2,2',3,5,6,7-octahydro-3-(1-methylethenylspiro[4H-azepine-4,3'-[3H]-indole]-2',7-dione, (3S,4R,5R)-6'-bromo-3-(3-chlorophenyl))-1,1',2,2',3,5,6,7-octahydro-5-(1-methylethenylspiro[4H-azepine-4,3'-[3H]-indole]-2',7-dione and (3R,4S,5S)-6'-bromo-3-(3-chlorophenyl)-1,1',2,2',3,5,6,7-octahydro-5-(1-methylethenyl)-spiro[4H-azepine-4,3'-[3H]-indole]-2',7-dione

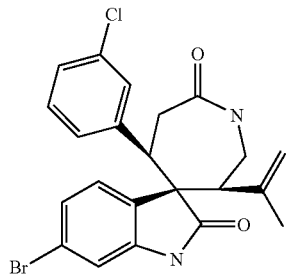

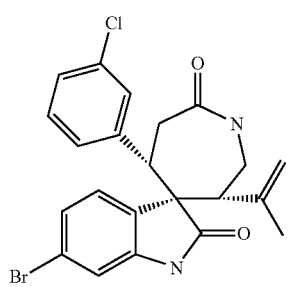

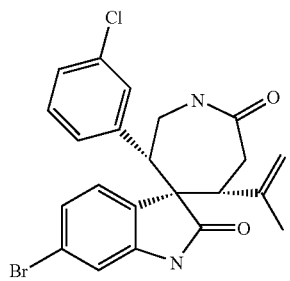

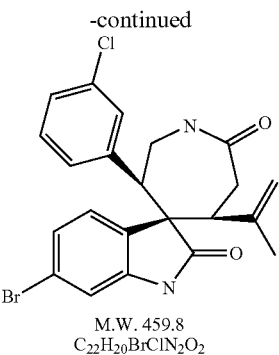

M.W. 459.8
C$_{22}$H$_{20}$BrClN$_2$O$_2$

Step 1

Preparation of Rac-(1S,2S,6S)-6'-bromo-2-(3-chlorophenyl)-6-(1-methylethenyl)-spiro[cyclohexane-1,3'-[3H]indole]-2',4(1'H)-dione

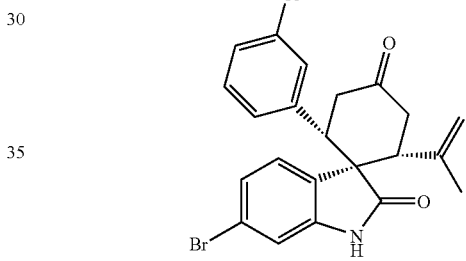

In a flask equipped with septum and stirring bar, a mixture of CuCl (0.11 g, 1.1 mmol) and Ph$_3$P (0.41 g, 1.1 mmol) was suspended in THF (20 mL). After stirring under argon at rt for 30 min, a THF solution (20 mL) of rac-(1R,2S)-6'-bromo-2-(3-chlorophenyl)-spiro[5-cyclohexene-1,3'-[3H]indole]-2',4(1'H)-dione (0.45 g, 1.1 mmol) prepared in Step 2 of Example 17 was added in one portion. After additional stirring for 10 min, isopropenylmagnesium bromide (0.5 M in ether, 11 mL, 5.6 mmol) was added dropwise to the resulting mixture during a period of 5 min at 0° C. After stirring under argon at 0° C. to −10° C. for 1 h, the reaction mixture was allowed to slowly warm to room temperature and stirred for 2 h. Sat.NH$_4$Cl was then added to the reaction mixture. The organic phase was separated. TLC and LC-MS analysis indicated the formation of the desired product and almost complete consumption of starting material. The mixture was then separated by flash column to give rac-(1S,2S,6R)-6'-bromo-2-(3-chlorophenyl)-4-(1-methylethenyl)-spiro[cyclohexane-1,3'-[3H]indole]-2',4(1'H)-dione (0.24 g, 49%) as a white solid: HRMS (ES$^+$) m/z Calcd for C$_{22}$H$_{19}$BrClNO$_2$+H [(M+H)$^+$]: 444.0361, Found: 444.0361.

Step 2

Preparation of Rac-E/Z-(1S,2S,6S)-6'-bromo-2-(3-chlorophenyl)-6-(1-methylethenyl)-spiro[cyclohexane-1,3'-[3H]indole]-2',4(1'H)-dione-4-oxime

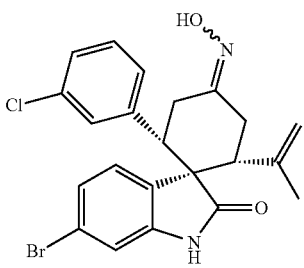

The suspension of rac-(1S,2S,6R)-6'-bromo-2-(3-chlorophenyl)-6-isopropenyl spiro[cyclohexane-1,3'-[3H]indole]-2',4(1'H)-dione (0.23 g, 0.52 mmol) and NH$_4$OH—HCl (0.1 g, 0.52 mmol) in EtOH-water (3/2, 20 mL) was allowed to reflux for 1 h. TLC analysis indicated the formation of desired product and complete consumption of starting material. The reaction was cooled to room temperature, and water was added. The mixture was extracted with ethyl acetate. The organic layer was separated, dried over MgSO$_4$, and concentrated. The residue was purified by chromatography (EtOAc:hexanes=1:2, then 1:1) to give the title compound as a white solid (0.18 g, 75%): HRMS (ES$^+$) m/z Calcd for C$_{22}$H$_{20}$BrClN$_2$O$_2$+H [(M+H)$^+$]: 459.0470, Found: 459.0470.

Step 3

Preparation of Rac-E/Z-(1S,2S,6S)-6'-bromo-2-(3-chlorophenyl)-6-iso-propenyl spiro[cyclohexane-1,3'-[3H]indole]-2',4(1'H)-dione-4-(O-p-toulenesulfonyl)-oxime

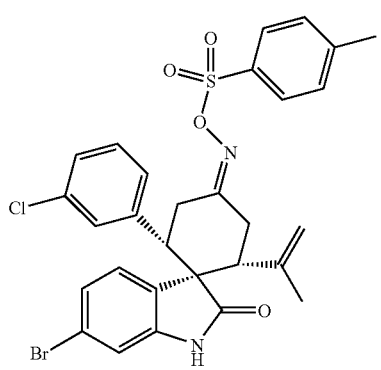

To the solution of rac-E/Z-(1S,2S,6S)-6'-bromo-2-(3-chlorophenyl)-6-iso-propenyl spiro[cyclohexane-1,3'-[3H]indole]-2',4(1'H)-dione-4-oxime (0.18 g, 0.39 mmol) and DMAP (0.1 g, 0.78 mmol) in dichloromethane (20 mL) was added a solution of p-toluenesulfonyl chloride (74 mg, 0.39 mmol) in dichloromethane (10 mL) at room temperature. The reaction mixture was stirred at room temperature for 1 h. The reaction was then concentrated and the residue was purified by chromatography (20%-40% AcOEt in hexanes) to give Rac-E/Z-(1S,2S,6S)-6'-bromo-2-(3-chlorophenyl)-6-iso-propenyl spiro[cyclohexane-1,3'-[3H]indole]-2',4(1'H)-dione-4-(O-p-toulenesulfonyl)-oxime as a white solid (0.12 g, 50%): HRMS (ES$^+$) m/z Calcd for C$_{29}$H$_{26}$BrClSN$_2$O$_4$+H [(M+H)$^+$]: 613.0558, Found: 613.0558.

Step 4

Rac-E/Z-(1S,2S,6S)-6'-bromo-2-(3-chlorophenyl)-6-isopropenyl spiro[cyclohexane-1,3'-[3H]indole]-2',4(1'H)-dione-4-(O-p-oulenesulfonyl-oxime) (0.1 g, 0.16 mmol) was dissolved in THF/H$_2$O (10/5 mL) and heated in a sealed tube under microwave irradiation at 100° C. for 25 min. After diluted with AcOEt the mixture was washed with water, dried over Na$_2$SO$_4$ and concentrated. The residue was purified by chromatography (EtOAc) to give the mixture of rac-(3'S,3R,5'R)-6-bromo-3'-(3-chlorophenyl)-5'-iso-propenyl spiro[3H-indole-3,4'-azopane]-2,7'(1'H)-dione and rac-(3'R,3R,5'S)-6-bromo-5'-(3-chlorophenyl)-3'-iso-propenyl spiro[3H-indole-3,4'-azopane]-2,7'(1'H)-dione as a white solid (81 mg). The mixture was further separated by chiral SFC to give (3S,4R,5R)-6'-bromo-5-(3-chlorophenyl)-1,1',2,2',3,5,6,7-octahydro-3-(1-methylethenyl)-spiro[4H-azepine-4,3'-[3H]-indole]-2',7-dione (HRMS (ES$^+$) m/z Calcd for C$_{22}$H$_{20}$BrClN$_2$O$_2$+H [(M+H)$^+$]: 459.0470, Found: 459.0470; (3R,4S,5S)-6'-bromo-5-(3-chlorophenyl))-1,1',2,2',3,5,6,7-octahydro-3-(1-methylethenylspiro[4H-azepine-4,3'-[3H]-indole]-2',7-dione: HRMS (ES$^+$) m/z Calcd for C$_{22}$H$_{20}$BrClN$_2$O$_2$+H [(M+H)$^+$]: 459.0470, Found: 459.0468; (3S,4R,5R)-6'-bromo-3-(3-chlorophenyl))-1,1',2,2',3,5,6,7-octahydro-5-(1-methylethenylspiro[4H-azepine-4,3'-[3H]-indole]-2',7-dione HRMS (ES$^+$) m/z Calcd for C$_{22}$H$_{20}$BrClN$_2$O$_2$+H [(M+H)$^+$]: 459.0470, Found: 459.0470; and (3R,4S,5S)-6'-bromo-3-(3-chlorophenyl)-1,1',2,2',3,5,6,7-octahydro-5-(1-methylethenyl)-spiro[4H-azepine-4,3'-[3H]-indole]-2',7-dione HRMS (ES$^+$) m/z Calcd for C$_{22}$H$_{20}$BrClN$_2$O$_2$+H [(M+H)$^+$]: 459.0470, Found: 459.0468.

Example 19

Preparation of rac-(3S,4R,5S)-6'-chloro-3-(3-chlorophenyl)-1,1',2,2',3,5,6,7-octahydro-5-methoxy-1-methyl-spiro[4H-azepine-4,3'-[3H]-indole]-2',7-dione (Scheme 3)

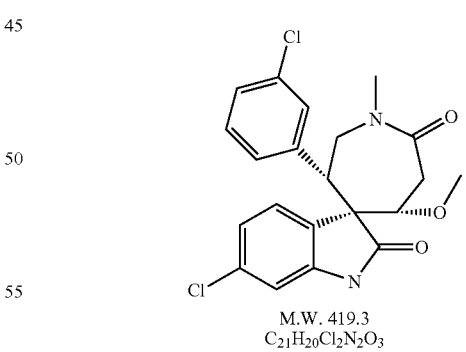

M.W. 419.3
C$_{21}$H$_{20}$Cl$_2$N$_2$O$_3$

Step 1

To a solution of rac-(1R,2S,6S)-6'-chloro-2-(3-chlorophenyl)-6-methoxy-spiro[cyclohexane-1,3'-[3H]indole]-2',4(1'H)-dione (500 mg, 1.28 mmole) was added NaH (60%, 52 mg, 1.28 mmole) at room temperature. After stirring for 30 min, dry THF (3 mL) was added and the reaction mixture was stirred for another 20 min. The reaction mixture was then cooled to 0° C., and a solution of 2-trimethylsilyl)ethoxymethyl chloride (213.0 mg, 1.28 mmole) in dry THF (2 mL) was added. After stirring at the same temperature for 30 min, the reaction mixture was quenched with sat NH4Cl, and extracted with ethyl acetate. The organic layer was separated, dried over MgSO$_4$, and concentrated. The residue was purified by chromatography to give rac-(1R,2S,6S)-6'-chloro-2-(3-chlorophenyl)-6-methoxy-1'-(2-trimethylsilanyl-ethoxymethyl)-spiro[cyclohexane-1,3'-[3H]indole]-2',4(1'H)-dione (370.0 mg, 57.0%).

Step 2

A suspension of rac-(1R,2S,6S)-6'-chloro-2-(3-chlorophenyl)-6-methoxy-1'-(2-trimethylsilanyl-ethoxymethyl)-spiro[cyclohexane-1,3'-[3H]indole]-2',4(1'H)-dione (360.0 mg, 0.69 mmol), NaOH (55.2 mg, 1.38 mmole) and NH$_2$OH—HCl (95.9 mg, 1.38 mmol) in EtOH-water (3/2, 15 mL) was allowed to reflux for 1.5 hrs. The reaction was cooled to room temperature, and water was added. The mixture was extracted with ethyl acetate. The organic layer was separated, dried over MgSO$_4$, and concentrated. The residue was purified by chromatography to give the corresponding oxime which was used in the next step without further purification.

Step 3

To the solution of rac-E/Z-spiro[cyclohexane-1,3'-[3H]indole]-2',4(1'H)-dione-4-oxime obtained above and DMAP (127.1 mg, 1.04 mmol) in dichloromethane (15 mL) was added a solution of p-toluenesulfonyl chloride (197.4 mg, 1.04 mmol) in dichloromethane (1 mL) at room temperature. The reaction mixture was stirred at room temperature for 1 h. The reaction was then concentrated and the residue was purified by column chromatography to give the corresponding E isomers of the spiro[cyclohexane-1,3'-[3H]indole]-2',4(1'H)-dione-4-(O-p-toulenesulfonyl)-oximes (110.5 mg, 22.7% in 2 steps) which was used in the next step without further purification.

Step 4

Rac-E-spiro[cyclohexane-1,3'-[3H]indole]-2',4(1'H)-dione-4-(O-p-toulenesulfonyl)-oxime (110.0 mg, 0.16 mmol) prepared in step 3 was dissolved in THF/H$_2$O (5/5 mL) and heated in a sealed tube under microwave irradiation at 90° C. for 20 min. After diluted with AcOEt the mixture was washed with water, dried over Na$_2$SO$_4$ and concentrated. The residue was purified by column chromatography to give rac-(3S,4R,5S)-6'-chloro-3-(3-chlorophenyl)-1,1',2,2',3,5,6,7-octahydro-5-methoxy-1'-(2-trimethylsilanyl-ethoxymethyl)-spiro[4H-azepine-4,3'-[3H]indole]-2',7-dione (58.3 mg, 69.7%)

Step 5

Rac-(3S,4R,5S)-6'-chloro-3-(3-chlorophenyl)-1,1',2,2',3,5,6,7-octahydro-5-methoxy-1'-(2-trimethylsilanyl-ethoxymethyl)-spiro[4H-azepine-4,3'-[3H]indole]-2',7-dione (54 mg, 1.0 mmol) was dissolved in DMF (2 mL) and NaH (60%, 8.0 mg, 0.2 mmole) was added at 0° C. After stirring at the same temperature for 10 min, MeI (71.0 mg, 0.5 mmole) was added by injection. The reaction mixture was allowed to stir at 0° C. to rt for 2 hrs. After diluted with AcOEt the mixture was washed with water, dried over Na2SO4 and concentrated. The residue was used in the next step without purification.

Step 6

The residue obtained above was dissolved in THF (10 mL) and TBAF (1.0 M, 0.4 mL) was added at rt. The reaction mixture was heated under refluxing for 16 hrs. After diluted with AcOEt the mixture was washed with water, dried over Na2SO4 and concentrated. The residue was purified by column chromatography to give rac-(3S,4R,5S)-6'-chloro-3-(3-chlorophenyl)-1,1',2,2',3,5,6,7-octahydro-5-methoxy-1-methyl-spiro[4H-azepine-4,3'-[3H]indole]-2',7-dione HRMS (ES$^+$) m/z Calcd for C$_{21}$H$_{20}$Cl$_2$N$_2$O$_3$+H [(M+H)$^+$]: 419.0924. Found: 419.0925.

Example 20

Preparation of rac-(3R,4R,5S)-6'-chloro-5-(3-chlorophenyl)-1,1',2,2',3,5,6,7-octahydro-3-methoxy-1-methyl-spiro[4H-azepine-4,3'-[3H]indole]-2',7-dione

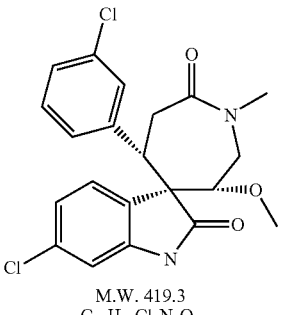

M.W. 419.3
C$_{21}$H$_{20}$Cl$_2$N$_2$O$_3$

In a manner similar to the method described in example 18, step 4-6 the rac-Z spiro[cyclohexane-1,3'-[3H]indole]-2',4(1'H)-dione-4-(O-p-toulenesulfonyl)-oxime (150.0 mg, 0.21 mmol) prepared in step 3 above was heated in a sealed tube under microwave irradiation at 90° C. for 20 min, followed by methylation, deprotection and purified by column chromatography to give rac-(3R,4R,5S)-6'-chloro-5-(3-chlorophenyl)-1,1',2,2',3,5,6,7-octahydro-3-methoxy-1-methyl-spiro[4H-azepine-4,3'-[3H]indole]-2',7-dione (48.0 mg): HRMS (ES$^+$) m/z Calcd for C$_{21}$H$_{20}$Cl$_2$N$_2$O$_3$+H [(M+H)$^+$]: 419.0924. Found: 419.0923.

Example 21

Preparation of rac-(3S,4R,5R)-6'-chloro-3-(3-chlorophenyl)-1-ethyl-1,1',2,2',3,5,6,7-octahydro-5-methoxy-spiro[4H-azepine-4,3'-[3H]indole]-2',7-dione

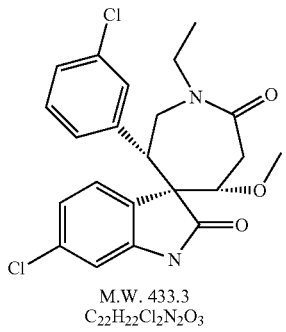

M.W. 433.3
C$_{22}$H$_{22}$Cl$_2$N$_2$O$_3$

In a manner similar to the method described in example 18, step 4-6 the rac-E spiro[cyclohexane-1,3'-[3H]indole]-2',4(1'H)-dione-4-(O-p-toulenesulfonyl)-oxime (100.0 mg, 0.14 mmol) prepared in step 3 above was heated in a sealed tube under microwave irradiation at 90° C. for 20 min, followed by ethylation, deprotection (50% TFA/CH$_2$Cl$_2$) and purified by column chromatography to give rac-(3S,4R,5R)-6'-chloro-3-(3-chlorophenyl)-1-ethyl-1,1',2,2',3,5,6,7-octahydro-5-methoxy-spiro[4H-azepine-4,3'-[3H]indole]-2',7-dione (26.0 mg, 60% in 3 steps):

HRMS (ES$^+$) m/z Calcd for C$_{22}$H$_{22}$Cl$_2$N$_2$O$_3$+H [(M+H)$^+$]: 433.1080. Found: 433.1081.

Example 22

Preparation of rac-(3R,4R,5S)-6'-chloro-5-(3-chlorophenyl)-1-ethyl-1,1',2,2',3,5,6,7-octahydro-3-methoxy-spiro[4H-azepine-4,3'-[3H]-indole]-2',7-dione

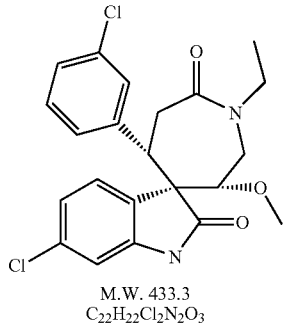

M.W. 433.3
$C_{22}H_{22}Cl_2N_2O_3$

In a manner similar to the method described in example 18, step 46, the rac-Z spiro[cyclohexane-1,3'-[3H]indole]-2',4 (1'H)-dione-4-(O-p-toulenesulfonyl)-oxime (225 mg, 0.32 mmol) prepared in step 3 above was heated in a sealed tube under microwave irradiation at 90° C. for 20 min, followed by ethylation, deprotection (50% TFA/CH₂Cl₂) and purified by column chromatography to give rac-(3R,4R,5S)-6'-chloro-5-(3-chlorophenyl)-1-ethyl-1,1',2,2',3,5,6,7-octahydro-3-methoxy-spiro[4H-azepine-4,3'-[3H]-indole]-2',7-dione (36.0 mg, 42% in 3 steps):

HRMS (ES⁺) m/z Calcd for $C_{22}H_{22}Cl_2N_2O_3$+H [(M+H)⁺]: 433.1080. Found: 433.1080.

Example 23

Preparation of (3S,4S,5R)-6'-chloro-5-(3-chlorophenyl)-3-ethoxy-1,1',2,2',3,5,6,7-octahydrospiro[4H-azepine-4,3'-[3H]-indole]-2',7-dione, (3R,4R,5S)-6'-chloro-5-(3-chlorophenyl)-3-ethoxyl-1,1',2,2',3,5,6, 7-octahydrospiro[4H-azepine-4,3'-[3H]-indole]-2',7-dione, (3S,4R,5S)-6'-chloro-3-(3-chlorophenyl)-5-ethoxy-1,1',2,2',3,5,6,7-octahydrospiro[4H-azepine-4,3'-[3H]-indole]-2',7-dione and (3R,4S,5R)-6'-chloro-3-(3-chlorophenyl)-5-ethoxy-1,1',2,2',3,5,6,7-octahydrospiro[4H-azepine-4,3'-[3H]-indole]-2',7-dione

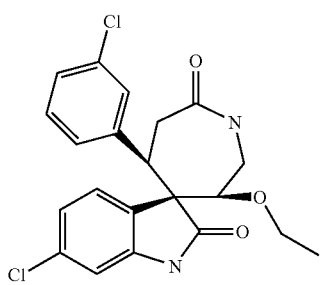

-continued

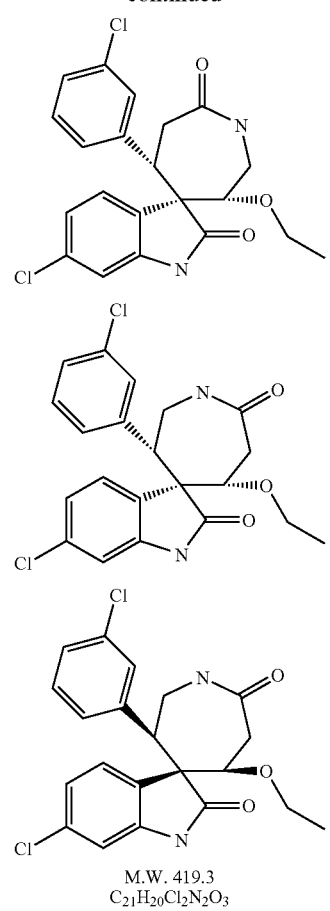

M.W. 419.3
$C_{21}H_{20}Cl_2N_2O_3$

Preparation of (3-ethoxy-1-methylene-allyloxy)-trimethyl-silane

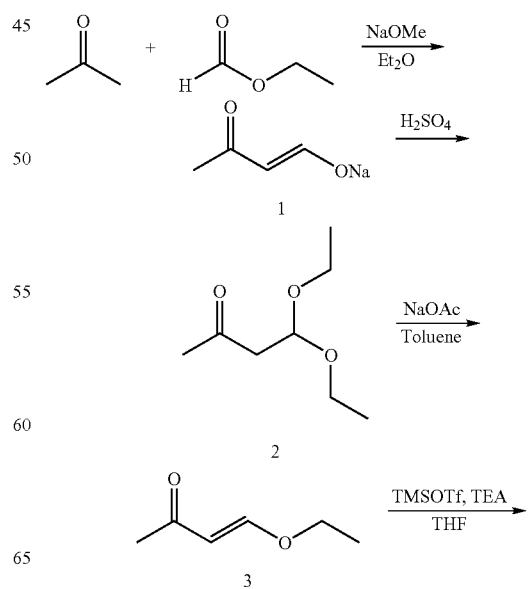

-continued

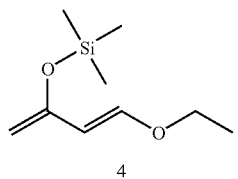

4

Step 1 and Step 2

In a three necked flask fitted with a Hershberg stirrer sealed by a lubricated rubber sleeve, a dropping funnel, and a reflux condenser attached to a calcium chloride drying tube placed 46.5 g of sodium methoxide (0.86 mmole, 1.0 eq) and 1 L of ether. The flask is cooled in an ice bath, and a mixture of 46.2 g of acetone (0.8 mmole, 1 eq) and 59.2 g of ethyl formate (0.8 mmole, 1 eq) is added through the dropping funnel at a rate of about 2 drops per second with stirred during a period of about 1 hour. Stirring is continued 15 minutes longer with the ice bath in place and then 1 hour after it is removed. After the product 1 was formed checked by NMR, ether was removed. Then the solid was dissolved in 1 L of EtOH, which was cooled in an ice bath, and 40 ml of $H_2SO_4$ in 500 ml of EtOH was added though the dropping funnel with stirring. After addition, the mixture was stirred at rt. overnight. Then neutralized with a EtOH Soln. of 3M KOH, and the salts were filtered off. The solvent was removed under normal pressure, then 33 g product 2. (Yield: 26%) was obtained under reduce pressure Bp: 60~80° C./<1 mbar. (Actually we get 43 g products which include 10 g of Ethanol! Checked by NMR)

Step 3

In a 100 mL flask, 24 g of 4,4-diethoxy-butan-2-one (150 mmol, 1 eq) (Actually including 5.5 g of Ethanol) was mixed with 25 ml of toluene. The mixture was heated to distill the solvent until the boiling point of distillate was higher than 107° C. After cooling, the mixture was divided into 10 tubes. Every tube was added 1.3 g of sodium diacetate (15 mmol, 1 eq) and 2 g of acetone, and then the tubes were sealed and the mixture was heated at 180° C. by microwave for 1 hour. Checked by NMR, the reaction went smoothly, only about less than 10% starting material left. After filtration, most solvent was removed under normal pressure. Distillation of the residue under reduce pressure to give 7.9 g pure product 3 (Yield: 60%) by Bp: 60~80° C./<1 mbar. (Actually we get 15.8 g crude products which include 7.9 of Toluene! Checked by NMR)

Step 4

In a 250 mL three-necked flask under N2 atomsphere, to a solution of 7.2 g of 4-ethoxy-but-3-en-2-one (63 mmol, 1 eq) and 12.7 g of TEA (126 mmol, 2 eq) in THF at −78° C., was added 21 g of TMSOTf (95 mmol, 1.5 eq) dropwise in 40 mins. Stirring was continued for 60 mins at 0~−30° C. After the conversion was complete (check by NMR), the reaction was quenched with 5% $NaHCO_3$, extract with Hexane and dried over $Na_2SO_4$. After remove the solvent the crude product was purified with redistillation (oil pump, <<1 mmbar: Bp, 40° C., Toluene; Bp, 115° C., product) to give 9.1 g pure product. Yield: 72.2%.

Preparation of rac-(1R,2S,6R)-6'-chloro-2-(3-chlorophenyl)-6-ethoxy-spiro[cyclohexane-1,3'-[3H]indole]-2',4(1'H)-dione To a suspension of E/Z-6-chloro-3-(3-chloro-benzylidene)-1,3-dihydro-indol-2-one (1.45 g, 15.0 mmol) in toluene (20 mL) in a sealed tube was added (3-ethoxy-1-methylene-allyloxy)-trimethyl-silane (1.24 g, 7.5 mmol). The reaction mixture was allowed to stir at 140° C. for 16 hrs. The solvent was removed by concentration. The residue was dissolved in MeOH (50 mL) and treated with 4 N NaOH (5 mL) at rt for 0.5 h. The reaction mixture was then diluted with AcOEt and washed with water and brine. After concentration the residue was purified by flash column (5%-30% AcOEt in Hex) to give a mixture (1.2 g) of rac-(1R,2R)-6'-chloro-2-(3-chlorophenyl)spiro[5-cyclohexene-1,3'-[3H]indole]-2',4(1'H)-dione and rac-(1R,2S,6R)-6'-chloro-2-3-chlorophenyl)-6-ethoxy-spiro[cyclohexane-1,3'-[3H]indole]-2',4(1'H)-dione (0.46 g, 18.6%) as white amorphous which was used for next steps without further purification. A small amount mixture was separated by normal phase HPLC gave rac-(1R,2S,6R)-6'-chloro-2-(3-chlorophenyl)-6-ethoxy-spiro[cyclohexane-1,3'-[3H]indole]-2',4(1'H)-dione. $MS^+$:358 (M+1).

In a manner similar to the method described in example 2 (method B), rac-(1R,2S,6R)-6'-chloro-2-(3-chlorophenyl)-6-ethoxy-spiro[cyclohexane-1,3'-[3H]indole]-2',4(1'H)-dione (150.0 mg, 0.34 mmole) was reacted with $NH_2OH$—HCl (119.5 mg, 1.72 mmol), NaOH (68.8 mg, 1.72 mmole) in EtOH-water (3/2, 10 mL) at refluxing for 2 hrs, followed by reacting with p-oluenesulfonyl chloride (133.1 mg, 0.70 mmol) in dichloromethane (10 mL) at room temperature for 2 hrs, and heating under microwave irradiation at 90° C. for 20 min. After diluted with AcOEt the mixture was washed with water, dried over $Na_2SO_4$ and concentrated. The residue was purified by chiral column chromatography to give (3S,4S,5R)-6'-chloro-5-(3-chlorophenyl)-3-ethoxy-1,1',2,2',3,5,6,7-octahydrospiro[4H-azepine-4,3'-[3H]-indole]-2',7-dione (10.2 mg), (3R,4R,5S)-6'-chloro-5-(3-chlorophenyl)-3-ethoxyl-1,1',2,2',3,5,6,7-octahydrospiro[4H-azepine-4,3'-[3H]-indole]-2',7-dione (10.8 mg), (3S,4R,5S)-6'-chloro-3-(3-chlorophenyl)-5-ethoxy-1,1',2,2',3,5,6,7-octahydrospiro[4H-azepine-4,3'-[3H]-indole]-2',7-dione (3.8 mg) and (3R,4S,5R)-6'-chloro-3-(3-chlorophenyl)-5-ethoxy-1,1',2,2',3,5,6,7-octahydrospiro[4H-azepine-4,3'-[3H]-indole]-2',7-dione (3.6 mg).

Example 24

Preparation of 3R,4S,5R)-6'-chloro-3-(3-chlorophenyl)-5-(2,2-dimethylpropoxy)-1,1',2,2',3,5,6,7-octahydrospiro[4H-azepine-4,3'-[3H]-indole]-2',7-dione, (3S,4R,5S)-6'-chloro-3-(3-chlorophenyl)-5-(2,2-dimethylpropoxy)-1,1',2,2',3,5,6,7-octahydrospiro[4H-azepine-4,3'-[3H]-indole]-2',7-dione, (3R,4R,5S)-6'-chloro-5-(3-chlorophenyl)-3-(2,2-dimethylpropoxy)-1,1',2,2',3,5,6,7-octahydrospiro[4H-azepine-4,3'-[3H]-indole]-2',7-dione and (3S,4S,5R)-6'-chloro-5-(3-chlorophenyl)-5-(2,2-dimethylpropoxy)-1,1',2,2',3,5,6,7-octahydrospiro[4H-azepine-4,3'-[3H]-indole]-2',7-dione

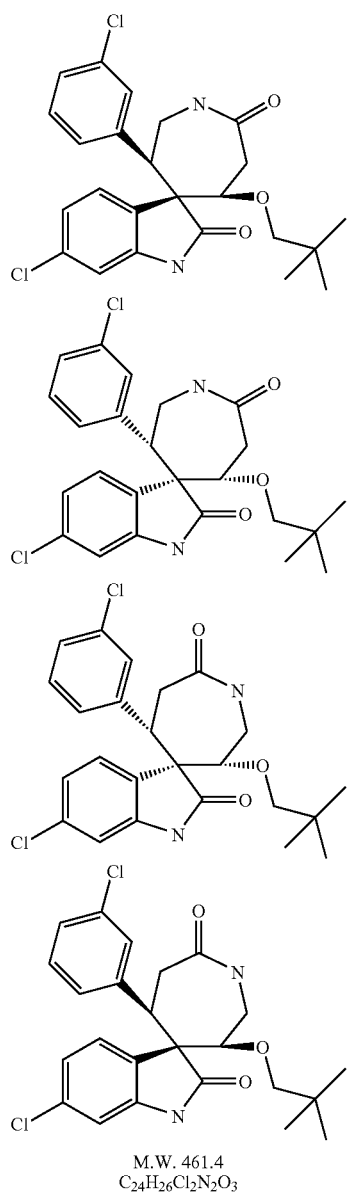

M.W. 461.4
C{24}H{26}Cl{2}N{2}O{3}

Step 1

Preparation of intermediate (E)-4-(2,2-Dimethylpropoxy)but-3-en-2-one (38192-200-1)

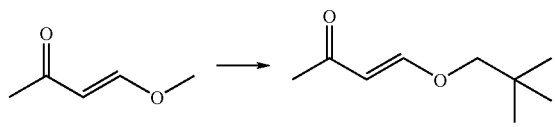

House vacuum was applied to a mixture of 4-methoxy-3-buten-2-one (14.0 g, 140 mmol) (Fisher Scientific), neopentyl alcohol (18.0 g. 200 mmol), pyrimidium p-toluenesulfonate (0.45 g, 1 mmol) and toluene (50 mL). This was stirred at 25-30° C. for 14 h. All solvent and volatiles were removed by vacuum and the residue was dissolved in hexane (75 mL). This was purified by chromatography (30% ethyl acetate/hexane) to give (E)-4-(2,2-dimethylpropoxy)but-3-en-2-one.

Step 2

Preparation of [(E)-3-(2,2-Dimethylpropoxy)-1-methyleneallyloxy]trimethylsilane (38192-200-2)

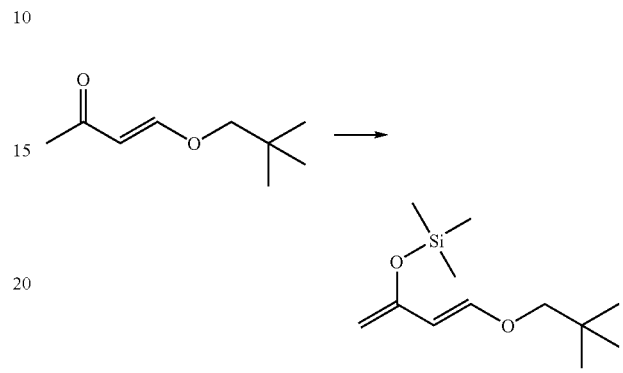

(E)-4-(2,2-dimethylpropoxy)but-3-en-2-one (14 g, 90 mmol) and triethylamine (10 g, 101 mmol) were combined in ethyl ether (200 mL). Trimethylsilyl trifluoromethanesulfonate (20 g, 90 mmol) (Aldrich) in carbon tetrachloride (30 mL) was added at −5° C. over 0.5 hr. This was stirred for 0.5 hr at 0° C. This was poured into cold 5% sodium bicarbonate (50 mL) and the organics were extracted into hexane. This was washed with saturated aqueous sodium chloride, dried (MgSO$_4$), and evaporated to give 21 g of [(E)-3-(2,2-dimethylpropoxy)-1-methylene-allyloxy]trimethylsilane.

Step 3

Preparation of rac-(1R,2S,6R)-6'-chloro-2-(3-chlorophenyl)-6-(2,2-dimethylpropoxy)-spiro[cyclohexane-1,3'-[3H]indole]-2',4(1'H)-dione

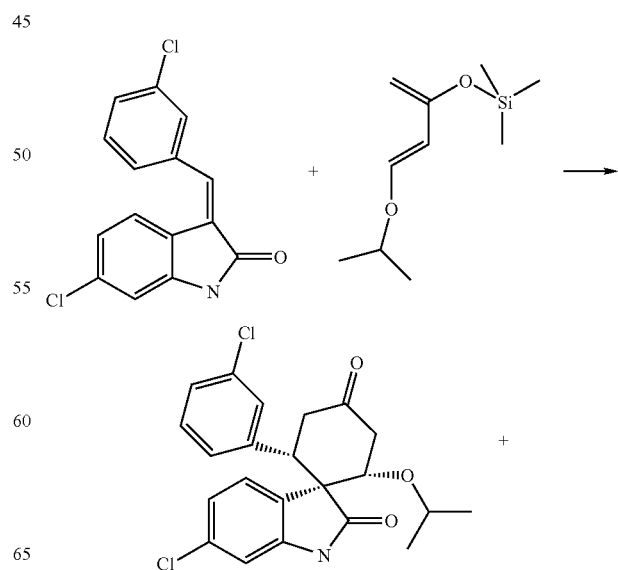

-continued

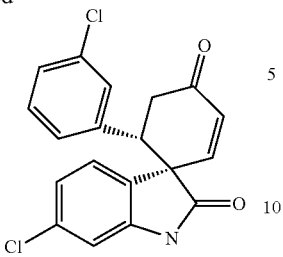

A mixture of E/Z-6-chloro-3-(3-chloro-benzylidene)-1,3-dihydro-indol-2-one (0.50 g, 1.72 mmol) and [(E)-3-(2,2-Dimethylpropoxy)-1-methyleneallyloxy]trimethylsilane (1.1 g, 5.5 mmole) in a sealed tube was heated to 150° C. for 1.5 hrs. The reaction mixture was diluted with MeOH (10 mL) and treated with 2.0 mL of 4 N NaOH at rt for 1 h. The mixture was then diluted with AcOEt and washed with Sat NH4Cl, brine, dried over Na2SO4. After concentration the residue was purified by flash column (2%-25% AcOEt in Hex) to give rac-(1R,2S,6R)-6'-chloro-2-(3-chlorophenyl)-6-(2,2-dimethylpropoxy)-spiro[cyclohexane-1,3'-[3H]indole]-2',4(1'H)-dione (310.4 mg, 43.1%) and rac-(1R,2S)-6'-chloro-2-(3-chlorophenyl)spiro[5-cyclohexene-1,3'-[3H] indole]-2',4(1'H)-dione (201.2 mg, 32.3%).

Step 4

In a manner similar to the method described in example 2 (method B), rac-(1R,2S,6R)-6'-chloro-2-(3-chlorophenyl)-6-(2,2-dimethylpropoxy)-spiro[cyclohexane-1,3'-[3H]indole]-2',4(1'H)-dione (167.0 mg, 0.37 mmole) was reacted with NH$_2$OH—HCl (52.0 mg, 0.74 mmol), NaOH (30.0 mg, 0.74 mmole) in EtOH-water (3/2, 7.5 mL) at refluxing for 1 h, followed by reacting with p-toluenesulfonyl chloride (102.0 mg, 0.51 mmol) in dichloromethane (10 mL) at room temperature for 2 hrs, and heating under microwave irradiation at 100° C. for 30 min. After diluted with AcOEt the mixture was washed with water, dried over Na$_2$SO$_4$ and concentrated. The residue was purified by chiral column chromatography to give 3R,4S,5R)-6'-chloro-3-(3-chlorophenyl)-5-(2,2-dimethylpropoxy)-1,1',2,2',3,5,6,7-octahydrospiro[4H-azepine-4,3'-[3H]-indole]-2',7-dione (11.0 mg): HRMS (ES$^+$) m/z Calcd for C$_{24}$H$_{26}$Cl$_2$N$_2$O$_3$+H [(M+H)$^+$]: 461.1393, Found: 461.1393; (3S,4R,5S)-6'-chloro-3-(3-chlorophenyl)-5-(2,2-dimethylpropoxy)-1,1',2,2',3,5,6,7-octahydrospiro[4H-azepine-4,3'-[3H]-indole]-2',7-dione (7.0 mg): HRMS (ES$^+$) m/z Calcd for C$_{24}$H$_{26}$Cl$_2$N$_2$O$_3$+H [(M+H)$^+$]: 461.1393, Found: 461.1393; (3R,4R,5S)-6'-chloro-5-(3-chlorophenyl)-3-(2,2-dimethylpropoxy)-1,1',2,2',3,5,6,7-octahydrospiro [4H-azepine-4,3'-[3H]-indole]-2',7-dione (7.0 mg): HRMS (ES$^+$) m/z Calcd for C$_{24}$H$_{26}$Cl$_2$N$_2$O$_3$+H [(M+H)$^+$]: 461.1393, Found: 461.1394; (3S,4S,5R)-6'-chloro-5-(3-chlorophenyl)-5-(2,2-dimethylpropoxy)-1,1',2,2',3,5,6,7-octahydrospiro[4H-azepine-4,3'-[3H]-indole]-2',7-dione (7.0 mg): HRMS (ES$^+$) m/z Calcd for C$_{24}$H$_{26}$Cl$_2$N$_2$O$_3$+H [(M+H)$^+$]: 461.1393, Found: 461.1394.

Example 25

Preparation of (3S,4S,5R)-6'-chloro-5-(3-chlorophenyl)-1,1',2,2',3,5,6,7-octahydro-3-(1-methylethoxy)-spiro[4H-azepine-4,3'-[3H]-indole]-2',7-dione, (3R,4R,5S)-6'-chloro-5-(3-chlorophenyl)-1,1',2,2',3,5,6,7-octahydro-3-(1-methylethoxy)-spiro[4H-azepine-4,3'-[3H]-indole]-2',7-dione, (3S,4R,5S)-6'-chloro-3-(3-chlorophenyl)-1,1',2,2',3,5,6,7-octahydro-5-(1-methylethoxy)-spiro[4H-azepine-4,3'-[3H]-indole]-2',7-dione and (3R,4S,5R)-6'-chloro-3-(3-chlorophenyl)-1,1',2,2',3,5,6,7-octahydro-5-(1-methylethoxy)-spiro[4H-azepine-4,3'-[3H]-indole]-2',7-dione

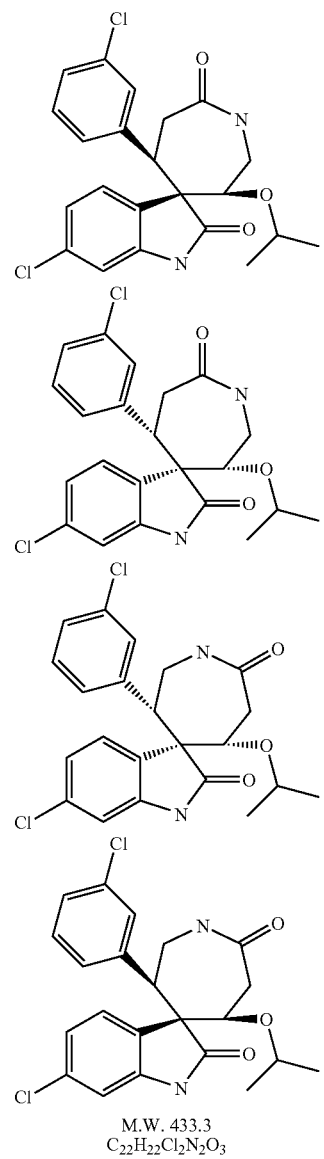

M.W. 433.3
C$_{22}$H$_{22}$Cl$_2$N$_2$O$_3$ (E)-4-Isopropoxy-but-3-en-2-one was prepared in the same manner as Example 24, Step 1 (38192-201-1)

((E)-3-Isopropoxy-1-methylene-allyloxy)-trimethylsilane was prepared in the same manner as Example 24, Step 2 (38192-201-1)

Rac-(1R,2S,6R)-6'-chloro-2-(3-chlorophenyl)-6-(1-methylethoxy)-spiro[cyclohexane-1,3'-[3H]indole]-2',4(1'H)-dione was prepared in the same manner as Example 24, Step 3

In a manner similar to the method described in example 2 (method A), rac-(1R,2S,6R)-6'-chloro-2-(3-chlorophenyl)-6-(1-methylethoxy)-spiro[cyclohexane-1,3'-[3H]indole]-2',4(1'H)-dione (138.0 mg, 0.33 mmole) was treated with NaN3 (54.0 mg, 0.83 mmole) in the presence of TiCl4 (1.0 M in $CH_2Cl_2$, 0.33 mL) (Aldrich) in acetonitrile (10 mL) at reflux for 6 hrs, followed by chiral chromatograph to give (3S,4S,5R)-6'-chloro-5-(3-chlorophenyl)-1,1',2,2',3,5,6,7-octahydro-3-(1-methylethoxy)-spiro[4H-azepine-4,3'-[3H]-indole]-2',7-dione (14.0 mg): HRMS ($ES^+$) m/z Calcd for $C_{22}H_{22}Cl_2N_2O_3$+H [(M+H)$^+$]: 433.1080, Found: 433.1080; (3R,4R,5S)-6'-chloro-5-(3-chlorophenyl)-1,1',2,2',3,5,6,7-octahydro-3-(1-methylethoxy)-spiro[4H-azepine-4,3'-[3H]-indole]-2',7-dione (14.0 mg): HRMS ($ES^+$) m/z Calcd for $C_{22}H_{22}Cl_2N_2O_3$+H [(M+H)$^+$]: 433.1080, Found: 433.1080;

(3S,4R,5S)-6'-chloro-3-(3-chlorophenyl)-1,1',2,2',3,5,6,7-octahydro-5-(1-methylethoxy)-spiro[4H-azepine-4,3'-[3H]-indole]-2',7-dione (9.0 mg): HRMS ($ES^+$) m/z Calcd for $C_{22}H_{22}Cl_2N_2O_3$+H [(M+H)$^+$]: 433.1080, Found: 433.1081; and (3R,4S,5R)-6'-chloro-3-(3-chlorophenyl)-1,1',2,2',3,5,6,7-octahydro-5-(1-methylethoxy)-spiro[4H-azepine-4,3'-[3H]-indole]-2',7-dione (12.0 mg): HRMS ($ES^+$) m/z Calcd for $C_{22}H_2Cl_2N_2O_3$+H [(M+H)$^+$]: 433.1080. Found: 433.1081.

Example 26

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$'s showing the biological activity of this invention exhibit activities less than about 10 μM.

What is claimed:

1. A compound of the formula

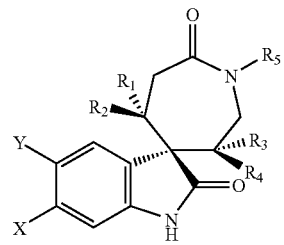

I wherein

X is selected from the group consisting of hydrogen, halogen, cyano, nitro, ethynyl and cyclopropyl, Y is hydrogen or fluoro, $R_1$, $R_2$, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_2$ or $R_3/R_4$ is hydrogen and the other not hydrogen, $R_5$ is selected from the group consisting of hydrogen, lower alkyl or substituted lower alkyl or a pharmaceutically acceptable salt thereof.

2. A compound of the formula

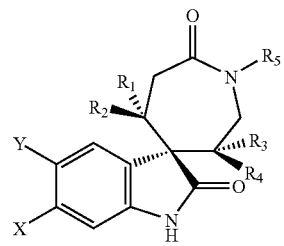

I wherein

X is halogen,

Y is hydrogen, $R_2$ is hydrogen, $R_4$ is hydrogen and $R_1$, and $R_3$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl, and substituted cycloalkenyl, with the proviso that one of $R_1/R_3$ is a meta-halogen substituted phenyl with or without further substitution $R_5$ is selected from the group consisting of hydrogen, lower alkyl or substituted lower alkyl or a pharmaceutically acceptable salt thereof.

3. A compound of the formula

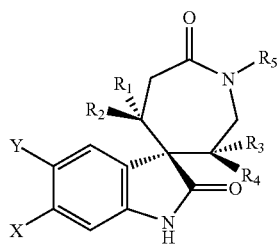

wherein
X is halogen,
Y is hydrogen,
R₂ is hydrogen,
R₄ is hydrogen and
one of R₁/R₃ is a meta-halogen substituted phenyl with or without further substitution and the other of R1/ R₃ is selected from the group consisting of lower alkyl, substituted lower alkyl, lower alkenyl, substituted lower alkenyl, aryl and substituted aryl,
R₅ is selected from the group consisting of hydrogen, lower alkyl and substituted lower alkyl
or a pharmaceutically acceptable salt thereof.

4. A compound of claim 1 selected from the group consisting of
rac-(3S,4R,5S)-6'-chloro-3-(3-chlorophenyl)-1,1',2,2',3,5,6,7-octahydro-5-methoxy-spiro[4H-azepine-4,3'-[3H]-indole]-2',7-dione,
rac-(3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione,
(3R,4S,5S)-6'-chloro-5-(3-chlorophenyl)-1,1',2,2',3,5,6,7-octahydro-3-(1-methylethenylspiro[4H-azepine-4,3'-[3H]-indole]-2',7-dione,
(3S,4R,5R)-6'-chloro-3-(3-chlorophenyl)-1,1',2,2',3,5,6,7-octahydro-5-(1-methylethenylspiro[4H-azepine-4,3'-[3H]-indole]-2',7-dione,
rac-(3S,4R,5R)-6'-chloro-3,5-bis-(3-chlorophenyl)-1,1',2,2',3,5,6,7-octahydrospiro[4H-azepine-4,3'-[3H]-indole]-2',7-dione,
(3R,4S,5S)-6'-chloro-5-(3-chlorophenyl)-1,1',2,2',3,5,6,7-octahydro-3(E)-(1-methyl-1-propenyl)-spiro[4H-azepine-4,3'-[3H]-indole]-2',7-dione,
(3S,4R,5R)-6'-chloro-3-(3-chlorophenyl)-1,1',2,2',3,5,6,7-octahydro-5(E)-(1-methyl-1-propenyl)-spiro[4H-azepine-4,3'-[3H]-indole]-2',7-dione,
rac-(3S,4R,5S)-6'-chloro-3-(4-chlorophenyl)-1,1',2,2',3,5,6,7-octahydro-5-methoxy-spiro[4H-azepine-4,3'-[3H]-indole]-2',7-dione,
rac-(3R,4R,5S)-6'-chloro-5-(4-chlorophenyl)-1,1',2,2',3,5,6,7-octahydro-3-methoxy-spiro[4H-azepine-4,3'-[3H]-indole]-2',7-dione and
(3R,4R,5S)-6'-chloro-5-(3-chlorophenyl)-1,1',2,2',3,5,6,7-octahydro-3-methoxy-spiro[4H-azepine-4,3'-[3H]-indole]-2',7-dione.

5. A compound of claim 1 selected from the group consisting of
(3S,4R,5R)-6'-chloro-3-(3-chlorophenyl)-1,1',2,2',3,5,6,7-octahydro-5-(3-methylphenyl)-spiro[4H-azepine-4,3'-[3H]-indole]-2',7-dione, (3R,4S,5S)-6'-chloro-5-(3-chlorophenyl)-1,1',2,2',3,5,6,7-octahydro-3-(3-methylphenyl)-spiro[4H-azepine-4,3'-[3H]-indole]-2',7-dione,
(3R,4S,5S)-6'-chloro-5-(3-chlorophenyl)-1,1',2,2',3,5,6,7-octahydro-3-(2-methylphenyl)-spiro[4H-azepine-4,3'-[3H]-indole]-2',7-dione,
(3S,4R,5R)-6'-chloro-3-(3-chlorophenyl)-1,1',2,2',3,5,6,7-octahydro-5-(2-methylphenyl)-spiro[4H-azepine-4,3'-[3H]-indole]-2',7-dione,
(3R,4S,5R)-6'-chloro-5-(3-chlorophenyl)-1,1',2,2',3,5,6,7-octahydro-3-(2-methylpropyl)-spiro[4H-azepine-4,3'-[3H]-indole]-2',7-dione,
(3S,4R,5S)-6'-chloro-3-(3-chlorophenyl)-1,1',2,2',3,5,6,7-octahydro-5-(2-methylpropyl)-spiro[4H-azepine-4,3'-[3H]-indole]-2',7-dione,
(3R,4S,5S)-6'-chloro-5-(3-chlorophenyl)-3-cyclopropyl-1,1',2,2',3,5,6,7-octahydrospiro[4H-azepine-4,3'-[3H]-indole]-2',7-dione,
(3S,4R,5R)-6'-chloro-3-(3-chlorophenyl)-5-cyclopropyl-1,1',2,2',3,5,6,7-octahydrospiro[4H-azepine-4,3'-[3H]-indole]-2',7-dione,
(3R,4S,5R)-6'-chloro-5-(3-chlorophenyl)-1,1',2,2',3,5,6,7-octahydro-3-(1-methylethyl)-spiro[4H-azepine-4,3'-[3H]-indole]-2',7-dione and
(3S,4R,5R)-6'-chloro-3-(3-chlorophenyl)-1,1',2,2',3,5,6,7-octahydro-5-(1-methylethyl)-spiro[4H-azepine-4,3'-[3H]-indole]-2',7-dione.

6. A compound of claim 1 selected from the group consisting of
(3R,4S,5S)-6'-chloro-5-(3-chlorophenyl)-3-(5-fluoro-2-methylphenyl)-1,1',2,2',3,5,6,7-octahydrospiro[4H-azepine-4,3'-[3H]-indole]-2',7-dione,
(3S,4R,5R)-6'-chloro-3-(3-chlorophenyl)-5-(5-fluoro-2-methylphenyl)-1,1',2,2',3,5,6,7-octahydrospiro[4H-azepine-4,3'-[3H]-indole]-2',7-dione,
(3R,4S,5S)-6'-chloro-5-(3-chlorophenyl)-1,1',2,2',3,5,6,7-octahydro-3-phenyl-spiro[4H-azepine-4,3'-[3H]-indole]-2',7-dione,
(3S,4R,5R)-6'-chloro-3-(3-chlorophenyl)-1,1',2,2',3,5,6,7-octahydro-3-phenyl-spiro[4H-azepine-4,3'-[3H]-indole]-2',7-dione,
rac-(3S,4R,5S)-6'-bromo-3-(3-chlorophenyl)-1,1',2,2',3,5,6,7-octahydro-5-methoxy-spiro[4H-azepine-4,3'-[3H]-indole]-2',7-dione,
rac-(3R,4R,5S)-6'-bromo-5-(3-chlorophenyl)-1,1',2,2',3,5,6,7-octahydro-3-methoxy-spiro[4H-azepine-4,3'-[3H]-indole]-2',7-dione,
(3R,4S,5S)-6'-bromo-5-(3-chlorophenyl))-1,1',2,2',3,5,6,7-octahydro-3-(1-methylethenylspiro[4H-azepine-4,3'-[3H]-indole]-2',7-dione,
(3S,4R,5R)-6'-bromo-3-(3-chlorophenyl))-1,1',2,2',3,5,6,7-octahydro-5-(1-methylethenylspiro[4H-azepine-4,3'-[3H]-indole]-2',7-dione,
rac-(3S,4R,5S)-6'-chloro-3-(3-chlorophenyl)-1,1',2,2',3,5,6,7-octahydro-5-methoxy-1-methyl-spiro[4H-azepine-4,3'-[3H]-indole]-2',7-dione and
rac-(3R,4R,5S)-6'-chloro-5-(3-chlorophenyl)-1,1',2,2',3,5,6,7-octahydro-3-methoxy-1-methyl-spiro[4H-azepine-4,3'-[3H]-indole]-2',7-dione.

7. A compound of claim 1 selected from the group consisting of
rac-(3S,4R,5R)-6'-chloro-3-(3-chlorophenyl)-1-ethyl-1,1',2,2',3,5,6,7-octahydro-5-methoxy-spiro[4H-azepine-4,3'-[3H]-indole]-2',7-dione,
rac-(3R,4R,5S)-6'-chloro-5-(3-chlorophenyl)-1-ethyl-1,1',2,2',3,5,6,7-octahydro-3-methoxy-spiro[4H-azepine-4,3'-[3H]-indole]-2',7-dione, (3R,4R,5S)-6'-chloro-5-(3-chlorophenyl)-3-ethoxyl-1,1',2,2',3,5,6,7-octahydrospiro[4H-azepine-4,3'-[3H]-indole]-2',7-dione, (3S,4R,5S)-6'-chloro-3-(3-chlorophenyl)-5-ethoxy-1,1',2,2',3,5,6,7-octahydrospiro[4H-azepine-4,3'-[3H]-indole]-2',7-dione, (3R,4R,5S)-6'-chloro-5-(3-chlorophenyl)-1,1',2,2',3,5,6,7-octahydro-3-(1-methylethoxy)-spiro[4H-azepine-4,3'-[3H]-indole]-2',7-dione, (3S,4R,5S)-6'-chloro-3-(3-chlorophenyl)-1,1',2,2',3,5,6,7-octahydro-5-(1-methylethoxy)-spiro[4H-azepine-4,3'-[3H]-indole]-2',7-dione, 3S,4R,5S)-6'-chloro-3-(3-chlorophenyl)-5-(2,2-dimethylpropoxy)-1,1',2,2',3,5,6,7-octahydrospiro[4H-azepine-4,3'-[3H]-indole]-2',7-dione and (3R,4R,5S)-6'-chloro-5-(3-chlorophenyl)-3-(2,2-dimethylpropoxy)-1,1',2,2',3,5,6,7-octahydrospiro[4H-azepine-4,3'-[3H]-indole]-2',7-dione.

8. A pharmaceutical formulation comprising a compound of the of the formula

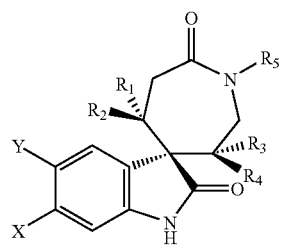

I wherein

X is selected from the group consisting of hydrogen, halogen, cyano, nitro, ethynyl and cyclopropyl, Y is hydrogen, $R_1$, $R_2$, $R_3$ and $R_4$ are selected from the group consisting of hydrogen, lower alkyl, lower alkoxyl, substituted lower alkyl, lower alkenyl, lower alkynyl, aryl, substituted aryl, heteroaryl, substituted heteroaryl, heterocycle, substituted heterocycle, cycloalkyl, substituted cycloalkyl, cycloalkenyl and substituted cycloalkenyl, with the proviso that one of $R_1/R_2$ or $R_3/R_4$ is hydrogen and the other not hydrogen, $R_5$ is hydrogen, lower alkyl or substituted lower alkyl, or a pharmaceutically acceptable salts thereof together with a pharmaceutically acceptable excipient.

* * * * *